United States Patent
Maurer, Jr. et al.

(10) Patent No.: US 7,590,219 B2
(45) Date of Patent: Sep. 15, 2009

(54) AUTOMATICALLY DETERMINING A BEAM PARAMETER FOR RADIATION TREATMENT PLANNING

(75) Inventors: Calvin R. Maurer, Jr., Mountain View, CA (US); Jay B. West, Mountain View, CA (US); John W. Allison, Los Altos, CA (US)

(73) Assignee: Accuray Incorporated, Sunnyvale, CA (US)

( * ) Notice: Subject to any disclaimer, the term of this patent is extended or adjusted under 35 U.S.C. 154(b) by 209 days.

(21) Appl. No.: 11/731,115

(22) Filed: Mar. 30, 2007

(65) Prior Publication Data

US 2008/0011945 A1   Jan. 17, 2008

Related U.S. Application Data

(60) Provisional application No. 60/790,503, filed on Apr. 7, 2006.

(51) Int. Cl.
*A61N 5/10* (2006.01)
(52) U.S. Cl. .................................. 378/65; 378/145
(58) Field of Classification Search ............ 378/65, 378/145–153
See application file for complete search history.

(56) References Cited

U.S. PATENT DOCUMENTS

| | | | |
|---|---|---|---|
| 5,278,886 A | 1/1994 | Kobiki et al. | 378/65 |
| 6,044,126 A | 3/2000 | Rousseau et al. | 378/65 |
| 6,546,073 B1 | 4/2003 | Lee | 378/65 |
| 6,741,674 B2 | 5/2004 | Lee | 378/65 |
| 7,096,055 B1 | 8/2006 | Schweikard | 600/407 |
| 2006/0023842 A1 | 2/2006 | Sohal et al. | 378/147 |
| 2006/0067481 A1 | 3/2006 | Morton | 378/151 |
| 2006/0074292 A1 | 4/2006 | Thomson et al. | 600/411 |
| 2006/0203964 A1 | 9/2006 | Nyholm et al. | 378/65 |
| 2007/0297565 A1 | 12/2007 | Wofford et al. | 378/65 |

FOREIGN PATENT DOCUMENTS

| | | |
|---|---|---|
| JP | 06-233831 | 8/1994 |
| WO | WO 2005/058419 | 6/2005 |

OTHER PUBLICATIONS

PCT International Search Report , International Application No. PCT/US 07/08657, Filed Apr. 6, 2007, Mailed Mar. 7, 2008, 5 Pages.
PCT Written Opinion of the International Searching Authority, International Application No. PCT/US 07/08657, Filed Apr. 6, 2007, Mailed Mar. 7, 2008, 4 Pages.
PCT International Search Report , International Application No. PCT/US 07/08656, Filed Apr. 6, 2007, Mailed Feb. 12, 2008, 4 Pages.
PCT Written Opinion of the International Searching Authority, International Application No. PCT/US 07/08656, Filed Apr. 6, 2007, Mailed Feb. 12, 2008, 6 Pages.
PCT International Preliminary Report on Patentability, PCT/US2007/008657 filed Apr. 6, 2007, mailed Oct. 16, 2008.

*Primary Examiner*—Courtney Thomas
(74) *Attorney, Agent, or Firm*—Blakely, Sokoloff, Taylor & Zafman LLP

(57) ABSTRACT

Systems and methods for automatically determining a beam parameter at each of a plurality of treatment nodes are disclosed. The beam parameter may include a beam shape, beam size and/or beam orientation. Systems and methods for automatically selecting multiple collimators in a radiation treatment system are also disclosed.

37 Claims, 20 Drawing Sheets

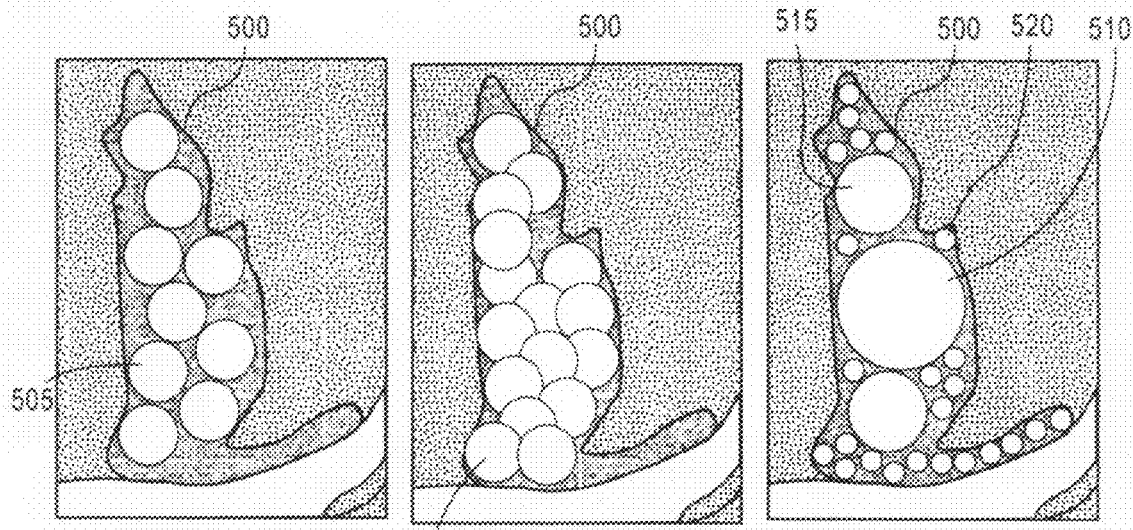
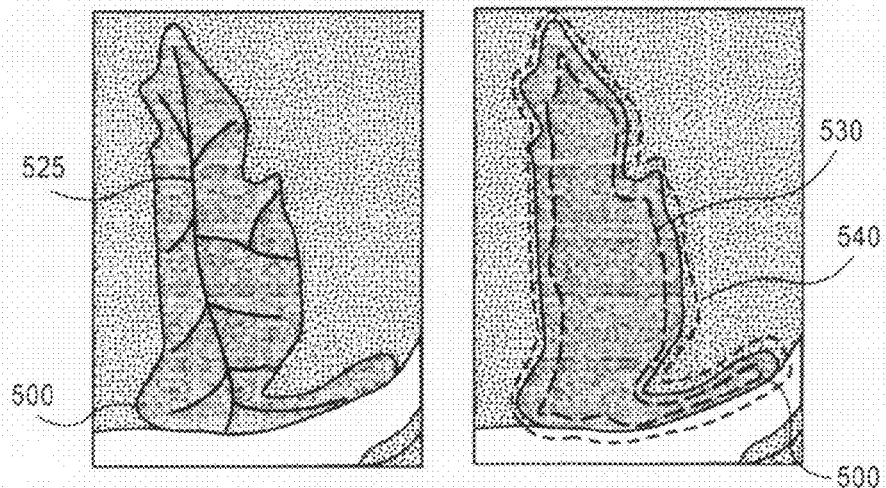
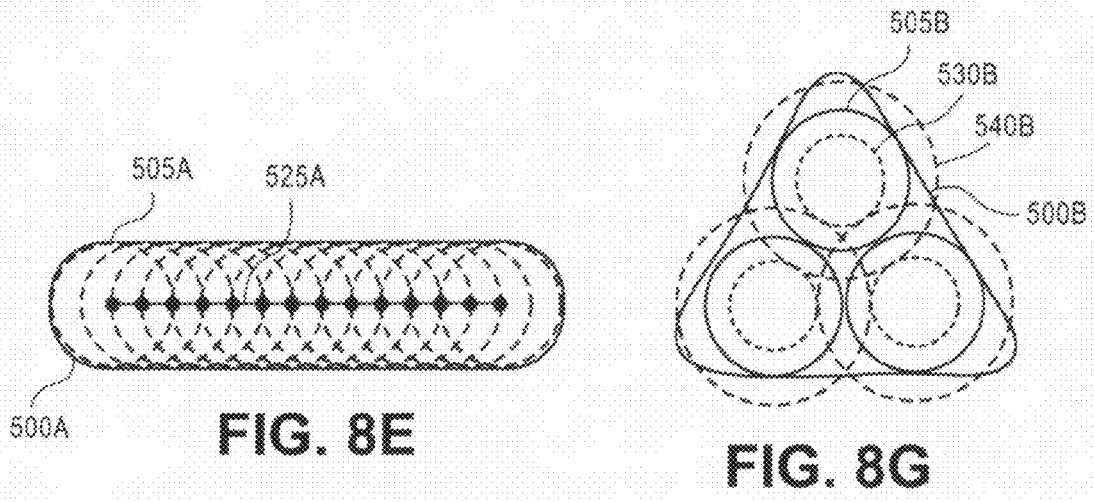

AUTOMATICALLY DETERMINING A BEAM PARAMETER FOR RADIATION TREATMENT PLANNING

CROSS-REFERENCE TO RELATED APPLICATIONS

This application claims priority to U.S. Provisional Patent Application No. 60/790,503, filed on Apr. 7, 2006, the entirety of which is hereby incorporated by reference.

FIELD

Embodiments of the present invention relate generally to radiation treatment and, more particularly, to treatment planning in radiation treatment.

BACKGROUND

Tumors and lesions are types of pathological anatomies characterized by abnormal growth of tissue resulting from the uncontrolled, progressive multiplication of cells, while serving no physiological function. Pathological anatomies can be treated with an invasive procedure, such as surgery, but this can be harmful and full of risks for the patient. A non-invasive method to treat a pathological anatomy (e.g., tumor, legion, vascular malformation, nerve disorder, etc.) is external beam radiation therapy. In one type of external beam radiation therapy, an external radiation source is used to direct a sequence of x-ray beams at a tumor site from multiple angles, with the patient positioned so the tumor lies in the path of the beam. As the angle of the radiation source changes, every beam passes through the tumor site, but passes through a different area of healthy tissue on its way to the tumor. As a result, the cumulative radiation dose at the tumor is high and the average radiation dose to healthy tissue is low.

The term "radiotherapy" refers to a radiation treatment procedure in which radiation is applied to a target region for therapeutic, rather than necrotic, purposes. The amount of radiation utilized in radiotherapy treatment sessions is typically about an order of magnitude smaller, as compared to the amount used in a radiosurgery session. Radiotherapy is typically characterized by a low dose per treatment (e.g., 100-200 centigray (cGy)), short treatment times (e.g., 10 to 30 minutes per treatment) and conventional or hyperfractionation (e.g., 30 to 45 days of treatment). For convenience, the term "radiation treatment" is used herein to mean radiosurgery and/or radiotherapy unless otherwise noted by the magnitude of the radiation.

In order to deliver a requisite dose to a targeted region, whilst minimizing exposure to healthy tissue and avoiding sensitive critical structures, a suitable treatment planning system is required. Treatment plans specify quantities such as the directions and intensities of the applied radiation beams, and the durations of the beam exposure. It is desirable that treatment plans be designed in such a way that a specified dose (required for the clinical purpose at hand) be delivered to a tumor, while avoiding an excessive dose to the surrounding healthy tissue and, in particular, to any important nearby organs. Developing an appropriate treatment planning system is especially challenging for tumors that are larger, have irregular shapes, or are close to a sensitive or critical structure.

A treatment plan may typically be generated from input parameters such as beam positions, beam orientations, beam shapes, beam intensities, and desired radiation dose constraints (that are deemed necessary by the radiologist in order to achieve a particular clinical goal). Sophisticated treatment plans may be developed using advanced modeling techniques, and state-of-the-art optimization algorithms.

Two kinds of treatment planning procedures are known: forward planning and inverse planning. In the early days of radiation treatment, treatment planning systems tended to focus on forward planning techniques. In forward treatment planning, a medical physicist determines the radiation dose duration, or beam-on time, and trajectory of a chosen beam and then calculates how much radiation will be absorbed by the tumor, critical structures (i.e., vital organs) and other healthy tissue. There is no independent control of the dose levels to the tumor and other structures for a given number of beams, because the radiation absorption in a volume of tissue is determined by the properties of the tissue and the distance of each point in the volume to the origin of the beam and the beam axis. More specifically, the medical physicist may "guess" or assign, based on his experience, values to various treatment parameters such as beam positions and beam intensities. The treatment planning system then calculates the resulting dose distribution. After reviewing the resulting dose distribution, the medical physicist may adjust the values of the treatment parameters. The system re-calculates a new resulting dose distribution. This process may be repeated, until the medical physicist is satisfied by the resulting dose distribution, as compared to his desired distribution. Forward planning tends to rely on the user's ability to iterate through various selections of beam directions and dose weights, and to properly evaluate the resulting dose distributions. The more experienced the user, the more likely that a satisfactory dose distribution will be produced.

Forward planning often utilizes an isocentric treatment process in which an external radiation source is used to direct a sequence of x-ray beams at a tumor target from multiple angles, with the patient being positioned so the tumor is at the center of rotation (isocenter) of the beams. In isocentric planning, each available beam is targeted at the same point to form the "isocenter," which generally may be a roughly spherical isodose region as represented by a sphere. Accordingly, isocentric planning may be often applied when treating a tumor that has a substantially regular (e.g., spherical) shape. The radiation beams are shaped by a device called a collimator. The collimator consists of dense material that is opaque to radiation, with the exception that there is a hollow portion through which radiation may pass. The shape and size of the radiation beam is then determined by the shape and size of this hollow portion (aperture). When we refer to "collimator size", we mean the size of radiation beam created by a given collimator configuration, as measured at a given distance from the radiation source. Hence the size of the sphere of radiation dose in isocentric planning may depend on the collimator size which may be, for example, about 30 millimeters as measured at about 800 millimeters from the radiation source. As the angle of the radiation source is changed, every beam passes through the tumor, but may pass through a different area of healthy tissue on its way to the tumor. To treat a target pathological anatomy, multiple dose spheres are superimposed or "stacked" on each other in an attempt to obtain a contour that closely matches the silhouette of the pathological anatomy. By stacking isocenters within a target volume, a plan may be developed that ensures that nearly all the target receives a sufficient dose. As a result, the cumulative radiation dose at the tumor may be high and the average radiation dose to healthy tissue may be low.

In gantry-based radiation treatment systems, the radiation beam may be shaped by a multileaf collimator (MLC), to conform to the silhouette of the target as seen from the orientation of the radiation beam source. The MLC is mounted on a gantry and coupled to a linear accelerator. The MLC includes several adjustable leaves which are able to block and/or filter radiation to vary the beam intensity and control distribution of the radiation. The leaves are typically made of a dense material (e.g., tungsten) that is essentially opaque to radiation, and are mechanically driven, individually, in and out of the radiation field of the beam to create a radiation field shape. FIG. 1 shows the leaves of an MLC adjusted to create a radiation field shape corresponding to a target silhouette. There are two conventional ways in which radiation treatment plans are generated for MLCs.

Most radiation delivery systems make use of a circular gantry surrounding the patient with a linear accelerator free to rotate within the circle. Multiple beams may be produced moving the accelerator around the circle; the trajectory of the beam can be characterized by a single angle describing the angle of rotation, called the "gantry angle". With conventional IMRT (Intensity Modulated Radiation Therapy) systems having an MLC, treatment planning is performed by, first, determining an optimal dose distribution at each node of the treatment system, i.e. each desired angle. After the dose distribution has been determined, field shapes are generated using a leaf sequencing algorithm, taking into account constraints of the MLC. That is, a set of instructions is generated to move the leaves in a given pattern, in order to achieve as closely as possible the optimum dose distribution. After the predicted dose distribution is calculated from the generated leaf sequencing algorithm, the radiation treatment of the target volume of interest ("VOI") occurs.

With conventional 3D conformal systems having an MLC, treatment planning is performed by first matching the leaves of the MLC to the target silhouette. In this case, there is no leaf sequencing algorithm, so the planning component seeks only to match the shape of each beam to the silhouette of the target from that gantry angle. Once the MLC positions have been determined, a predicted dose distribution may be generated, and the radiation treatment of the target VOI occurs.

Another mode of delivering radiation treatment is that provided by the CyberKnife® system. Instead of moving the radiation delivery device in a circle around the patient, it is mounted on a multi-jointed robotic manipulator that has freedom to make both translational and rotational movement. Hence, radiation may be delivered from a wide range of positions and orientations relative to the patient, instead of being restricted to angles chosen within the circular arc on which the gantry-mounted linac can travel.

BRIEF DESCRIPTION OF THE DRAWINGS

The present invention is illustrated by way of example and not limitation in the figures of the accompanying drawings, in which:

FIGS. 8A-8K are schematic views illustrating pre-optimization algorithms in accordance with embodiments of the invention;

DETAILED DESCRIPTION

Figure 1:
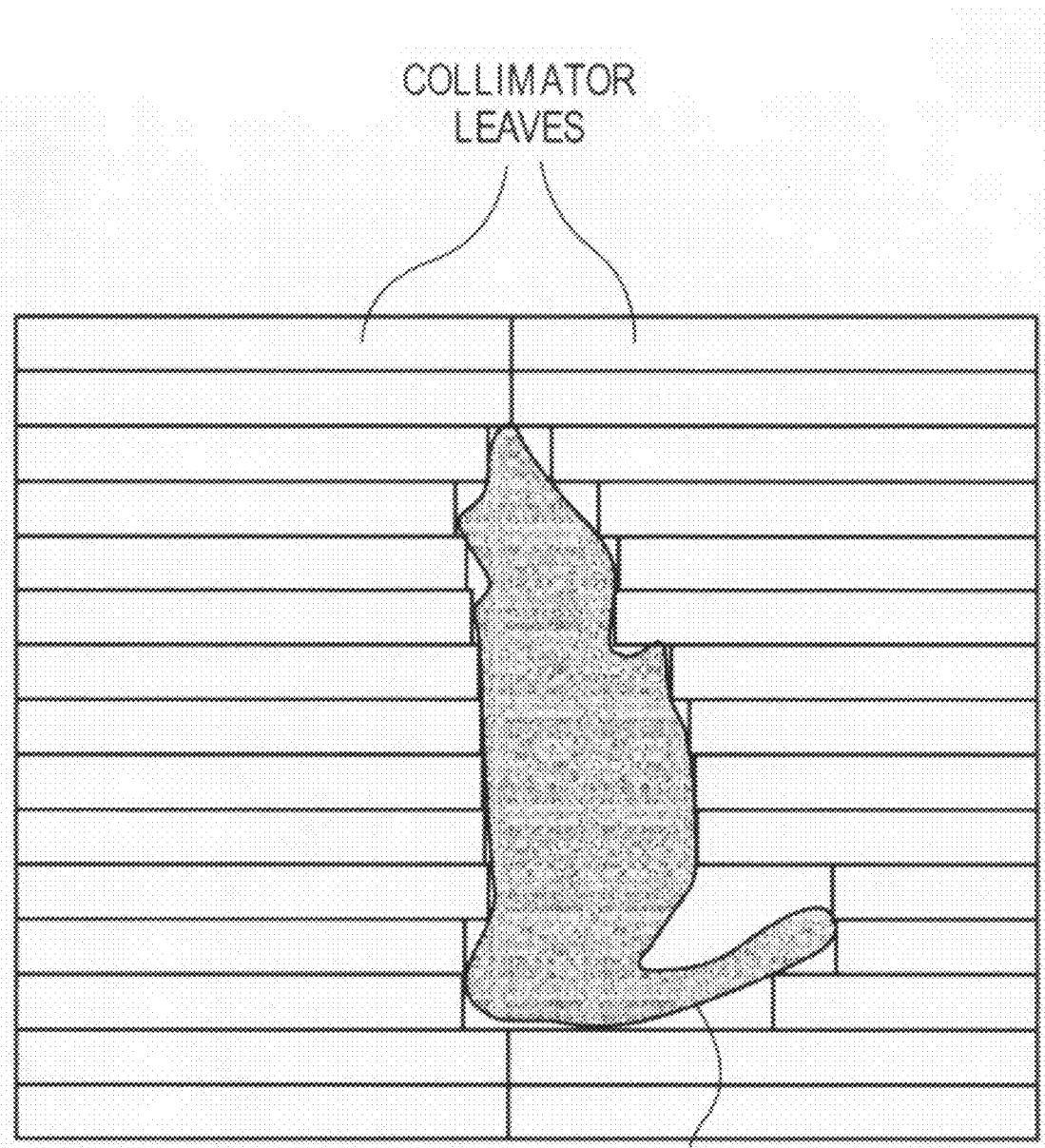
FIG. 1 is a plan view of a multileaf collimator adjusted to conform to a pathological anatomy.

In the following description, for purposes of explanation, numerous specific details are set forth in order to provide a thorough understanding of the present invention. It will be evident, however, to one skilled in the art that the present invention may be practiced without these specific details. In other instances, well-known circuits, structures, and techniques are not shown in detail or are shown in block diagram form in order to avoid unnecessarily obscuring an understanding of this description.

Reference in the description to "one embodiment" or "an embodiment" means that a particular feature, structure, or characteristic described in connection with the embodiment is included in at least one embodiment of the invention. The appearances of the phrase "in one embodiment" in various places in the specification do not necessarily all refer to the same embodiment.

An apparatus and method for automating the selection of one or more radiation beam parameters for a radiation treatment system are described. In one particular embodiment, the apparatus and method automatically selects a beam size. In another embodiment, the apparatus and method automatically determines the beam shape. In still another embodiment, the apparatus and method automatically determines the beam orientation. It will be appreciated that the apparatus and method may automatically determine combinations of the beam size, beam shape and beam orientation. Embodiments of the apparatus and method may also automatically select multiple collimators. Embodiments of the apparatus and method may also automatically select one or more collimators based on the automatically determined beam parameter(s).

In inverse planning, in contrast to forward planning, the medical physicist specifies a desired dose distribution, for example, the minimum dose to the tumor and the maximum dose to other healthy tissues, independently, and the treatment planning module then selects the direction, distance, and total number and intensity of the beams in order to achieve the specified dose conditions. Given a desired dose distribution specified and input by the user (e.g., the minimum and maximum doses), the inverse planning module selects and optimizes dose weights and/or beam directions, i.e. selects an optimum set of beams that results in such a distribution.

During inverse planning, volumes of interest (VOIs) are used to represent user-defined structures to be targeted or avoided with respect to the administered radiation dose. That is, the radiation source is positioned in a sequence calculated to localize the radiation dose into a VOI that represents the tumor requiring treatment, while as much as possible avoiding radiation dose to VOIs representing critical structures. Once the target (e.g., tumor) VOI has been defined, and the critical VOIs and soft tissue (all tissue within the treatment region that is represented by neither a target nor critical VOI) volumes have been specified, the responsible radiation oncologist or medical physicist specifies, for example, the minimum radiation dose to the target VOI and the maximum dose to normal and critical healthy tissue. The software then produces the inverse treatment plan, relying on the positional capabilities of the radiation treatment system, to meet the dose constraints of the treatment plan.

Figure 2:
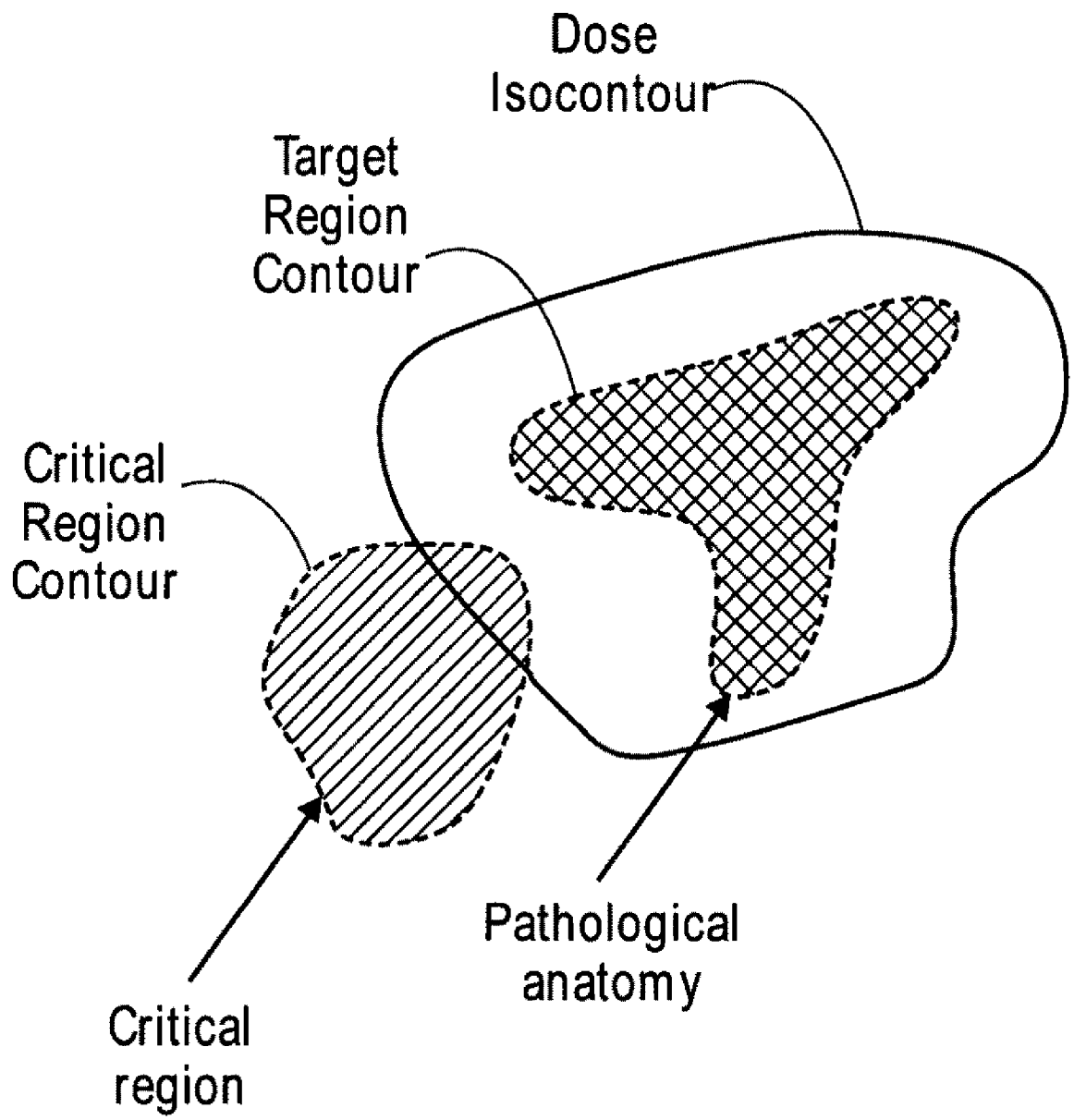
FIG. 2 is a schematic of a graphical output of a treatment planning software displaying a slice of a CT image.

FIG. 2 is a conceptual illustration of a graphical output of a treatment planning system displaying a slice of a CT image. The illustration of the CT image includes a pathological anatomy that is targeted for treatment, as well as a critical region that is positioned near the pathological anatomy. The treatment planning software enables the generation of a critical region contour around the critical region and a target region contour around the pathological anatomy. Conventionally, a user manually delineates points (e.g., some of the dots on the contour lines of FIG. 2) on the display that are used by the treatment planning software to generate the corresponding contours. While this may seem an easy task, such matching is difficult due to the three-dimensional nature and irregularities of pathological and normal anatomies. Based on specified minimum dose to the target region and the maximum dose to the critical region, the treatment planning software generates the dose isocontour for the target region. The dose isocontour is a line of constant dose, and represents either a given dose percentage (e.g., 60%, 70%, 80%, etc.) of a specified prescription dose for the target region, or an absolute dose value (e.g. 2000 centiGray). Ideally, the dose isocontour representing the minimum amount of dose deemed to be clinically effective should perfectly match the contour of the target region. In some cases, the dose isocontour generated by the treatment planning software is not optimal, and can include portions of the critical region, as illustrated in FIG. 2.

Figure 3:
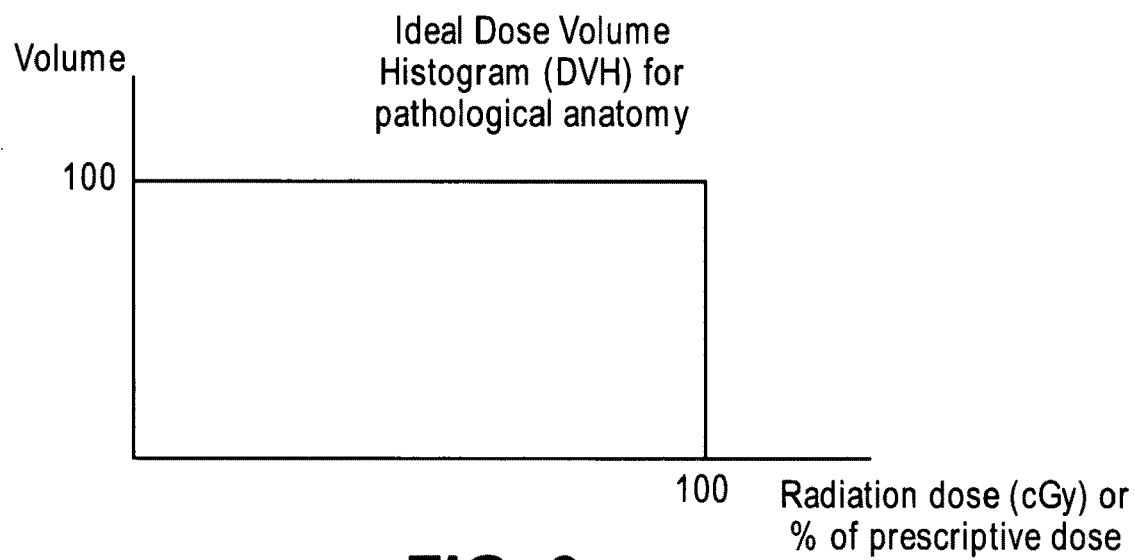
FIG. 3 is a graph showing an ideal DVH for a pathological anatomy.
Figure 4:
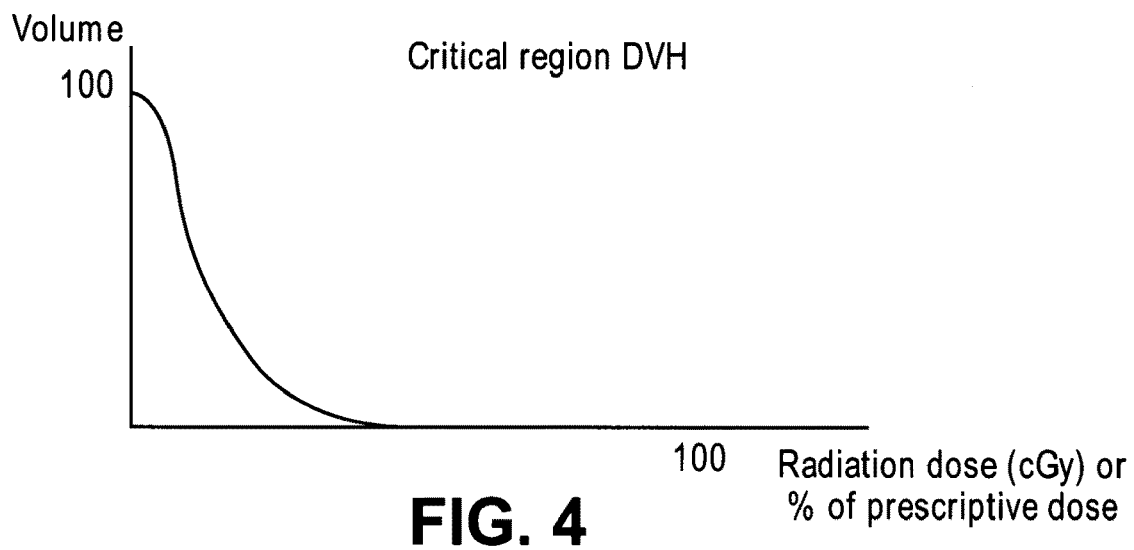
FIG. 4 is a graph showing a desirable DVH for a critical region.

Two of the principal requirements for an effective radiation treatment system are homogeneity and conformality. Homogeneity is the uniformity of the radiation dose over the volume of the target (e.g., pathological anatomy such as a tumor, lesion, vascular malformation, etc.) and can be characterized by a dose volume histogram (DVH). The DVH represents, on the y axis, a volume, either as an absolute measurement or a percentage of the VOI volume. On the x axis are dose values, either as absolute dose or as percentage of a given dose (e.g. maximum dose or prescription dose). The DVH graph shows how much volume of the VOI is covered by a dose greater than or equal to the corresponding dose value on the x axis. An ideal DVH for the pathological anatomy would be a rectangular function as illustrated in FIG. 3, where the dose is 100 percent of the prescribed dose over the volume of the pathological anatomy. A desirable DVH for a critical region would have the profile illustrated in FIG. 4, where the volume of the critical anatomical structures receives as little of the prescribed dose as possible.

Conformality is the degree to which the radiation dose matches (conforms to) the shape and extent of the target (e.g., tumor) in order to avoid damage to critical adjacent structures. More specifically, conformality is a measure of the amount of prescription (Rx) dose (amount of dose applied) within a target VOI. Conformality may be measured using a conformality index (CI)=total volume at≧Rx dose/target volume at≧Rx dose. Perfect conformality results in a CI=1. With conventional radiotherapy treatment, using treatment planning software, a clinician identifies a dose isocontour for a corresponding VOI for application of a treatment dose (e.g., 3000 cGy).

A goal of radiation treatment planning is to find a set of radiation beams including the position, shape, and "weight" (amount of radiation delivered by the beam) of each beam that produces a dose distribution that matches clinical objectives (such as minimum and maximum dose to target and critical structures, conformality, and homogeneity). In a robotic-based radiation treatment such as the CyberKnife® system, the radiation beam can be moved to a variety of positions and orientations relative to the patient.

Figure 5:
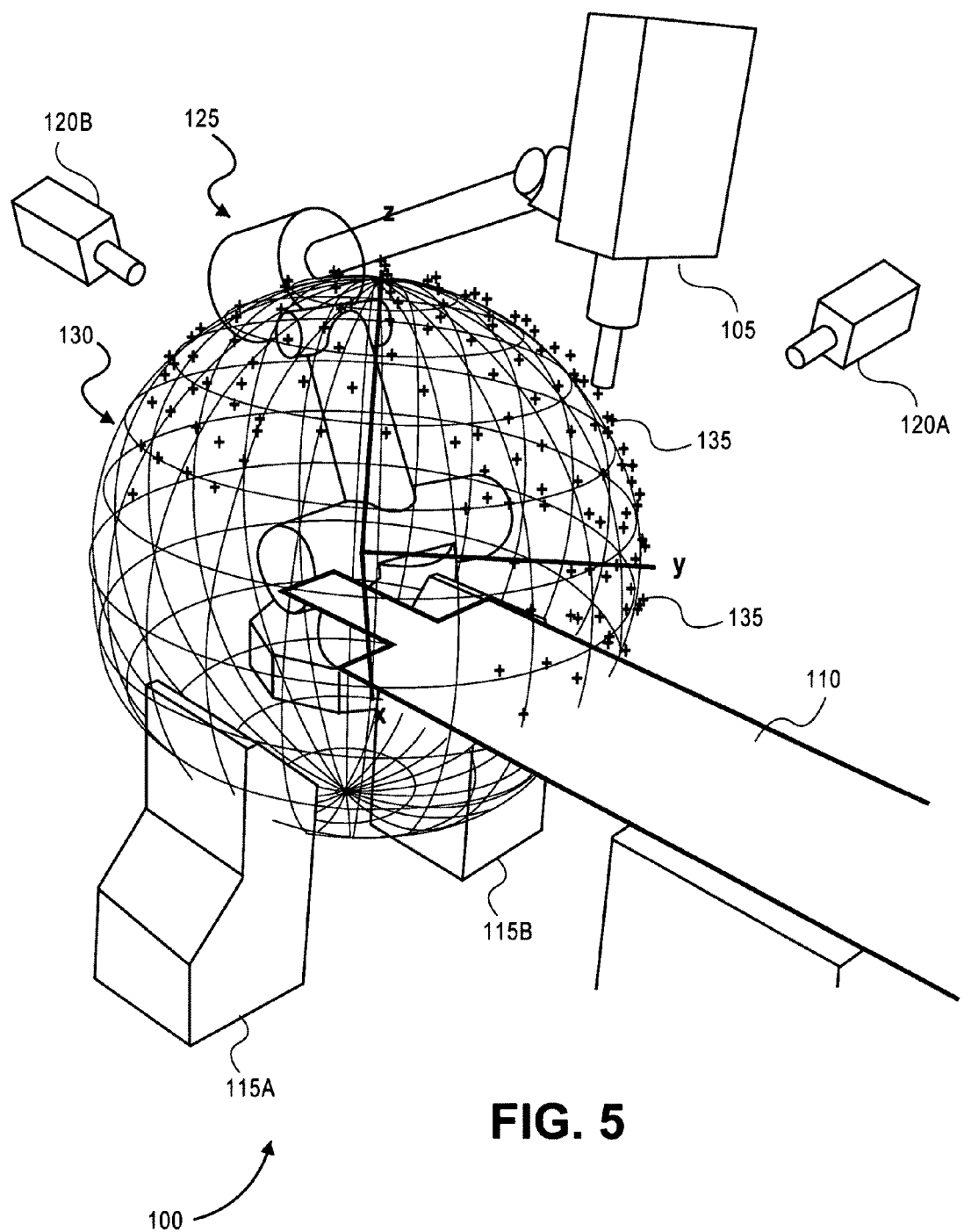
FIG. 5 is a perspective view of a radiation treatment system having spatial nodes in accordance with one embodiment of the invention.

FIG. 5 is a perspective view of a workspace of a radiation treatment delivery system 100 including a set of spatial nodes at which to position the radiation source, in accordance with an embodiment of the invention. The illustrated embodiment of radiation treatment delivery system 100 includes a radiation source 105, a treatment couch 110, detectors 115A and 115B (collectively 115, also referred to as imagers), imaging sources 120A and 120B (collectively 120), and a robotic arm 125.

Radiation treatment delivery system 100 may be used to perform radiation treatment (e.g., radiosurgery and/or radiotherapy) to treat or destroy a lesion (e.g., tumor tissue) within a patient. During radiation treatment, the patient rests on treatment couch 110, which is maneuvered to position a volume of interest ("VOI") describing a target to a preset position or within an operating range accessible to radiation source 105 (e.g., field of view). In one embodiment, radiation treatment delivery system 100 is an image guided radiation treatment delivery system. Together, imaging sources 120 and detectors 115 are an imaging guidance system that provides visual control over the position of treatment couch 110 and the patient thereon and the alignment of radiation source 105 with respect to the VOI within the patient. In one embodiment, treatment couch 110 may be coupled to a positioning system (not illustrated), such as a robotic arm, that receives feedback from the imaging guidance system to provide accurate control over both the displacement and orientation of the VOI within the patient relative to radiation source 105.

In one embodiment, robotic arm 125 has multiple (e.g., six) degrees of freedom capable of positioning radiation source 105 with almost an infinite number of possibilities within its operating envelope. Allowing this type of movement would result in several challenges. Firstly, a large number of positional possibilities creates a difficult problem to solve for a treatment planning system when determining beam positions and trajectories for treating a particular VOI. Secondly, allowing unconstrained movement within the operating envelope of robotic arm 125 may result in possible collisions between radiation source 105 and the patient or other stationary objects. These problems may be solved by limiting radiation source 105 to a finite number of spatial nodes from which radiation source 105 may emit a radiation beam and further creating specific paths (known safe paths) that robot arm 125 must follow between the spatial nodes.

A collection of spatial nodes and associated safe paths interconnecting these spatial nodes is called a "workspace" or "node set". FIG. 5 illustrates a workspace 130, including a number of spatial nodes 135 each represented by a "+" symbol (only a couple are labeled). Multiple different workspaces may be created and defined for different patient work areas. For example, workspace 130 may be spherical (as illustrated) and defined for treating VOIs residing within the head of a patient. Alternatively, workspace 130 may have other geometries (e.g., elliptical) and defined for treating VOIs residing within other areas of a patient. Additionally, multiple workspaces 130 may be defined for different portions of a patient, each having different radius or source to axis distances ("SAD"), such as 650 mm and 800 mm. The SAD is the distance between the electron target used for photon generation in radiation source 105 and the target described by the VOI. The SAD defines the surface area of the workspace. In one embodiment of an elliptical workspace, the SAD may range from 900 mm to 1000 mm. Other SADs may be used.

Spatial nodes 135 reside on the surface of workspace 130. Spatial nodes 135 represent positions where radiation source 105 is allowed to stop and deliver a dose of radiation to the VOI within the patient. During delivery of a treatment plan, robotic arm 125 moves radiation source 105 to each and every spatial node 135 following a predefined path. In one embodiment, even if a particular treatment plan does not call for delivery of a dose of radiation from a particular spatial node 135, radiation source 105 will still visit that particular spatial node 135, since it falls along a predetermined safe path. In other embodiments the robot may skip unused nodes using more detailed knowledge of allowable transitions between nodes.

FIG. 5 illustrates a complete node set including an exemplary number of spatial nodes 135. The complete node set may include spatial nodes 135 substantially uniformly distributed over the geometric surface of workspace 130. The complete node set includes all programmed spatial nodes 135 and provides a workable number of spatial nodes 135 for effectively computing treatment plan solutions for most ailments and associated VOIs. The complete node set provides a reasonably large number of spatial nodes 135 such that homogeneity and conformality thresholds can be achieved for a large variety of different VOIs, while providing enough vantage points to avoid critical structures within patients. It will be appreciated that the complete node set may include more or less spatial nodes 135 than is illustrated or discussed. For example, as processing power increases and experience gained creating treatment plans, the average number of spatial nodes 135 may increase with time to provide greater flexibility and higher quality treatment plans. In some embodiments, targets may have pre-defined spatial node sets based on their location. The sets are typically discovered through experience with similar targets in the same or similar locations.

Figure 6:
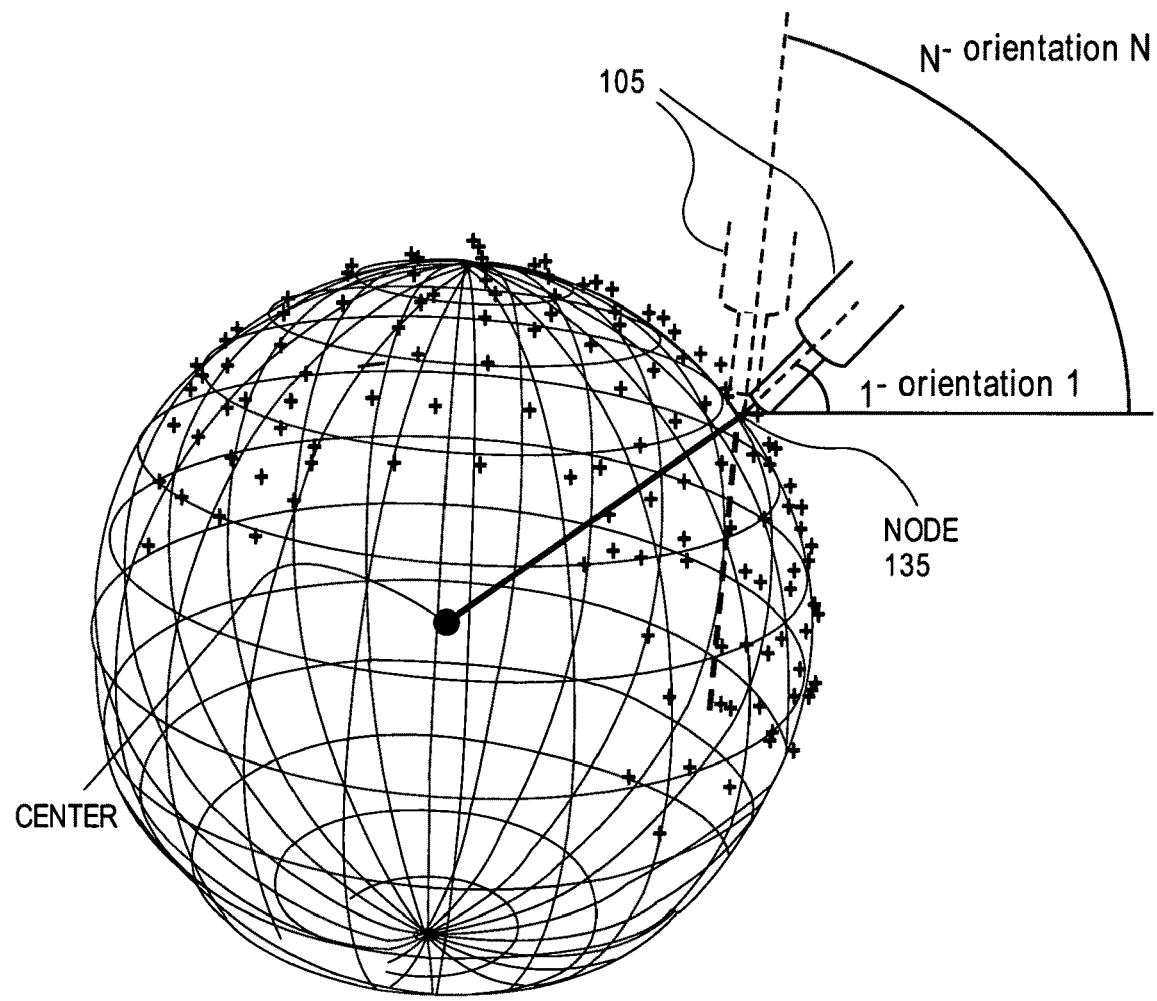
FIG. 6 is a perspective view of a collimator at different orientations in accordance with one embodiment of the invention.

FIG. 6 illustrates re-orientation of the radiation source 105 at a node. As explained above, the radiation source 105 can be positioned at any of the spatial nodes 135. In addition, at each node, the radiation source can be reoriented. For example, the radiation source 105 may be positioned at a first orientation (orientation 1) at an angle $\alpha_1$ at the node 135. The radiation source 105 may also be reoriented to any number of orientations at angle $\alpha_N$ at the same node 135. In one embodiment, the radiation source 105 can be reoriented to twelve different orientations at each node 135 (at twelve different angles $\alpha_1 \ldots \alpha_{12}$). It will be appreciated that the radiation source 105 can be reoriented to fewer orientations or more orientations. As shown in FIG. 6, one orientation (orientation 1) may deliver a radiation beam at an angle that passes through the center of the VOI. Other orientations may deliver radiation beams within the VOI, but not through the center of the VOI, and still other orientations may deliver radiation beams outside of the VOI. It will be appreciated that the treatment planning system may automatically eliminate the orientations that deliver radiation beams outside of the VOI.

Figure 7A:
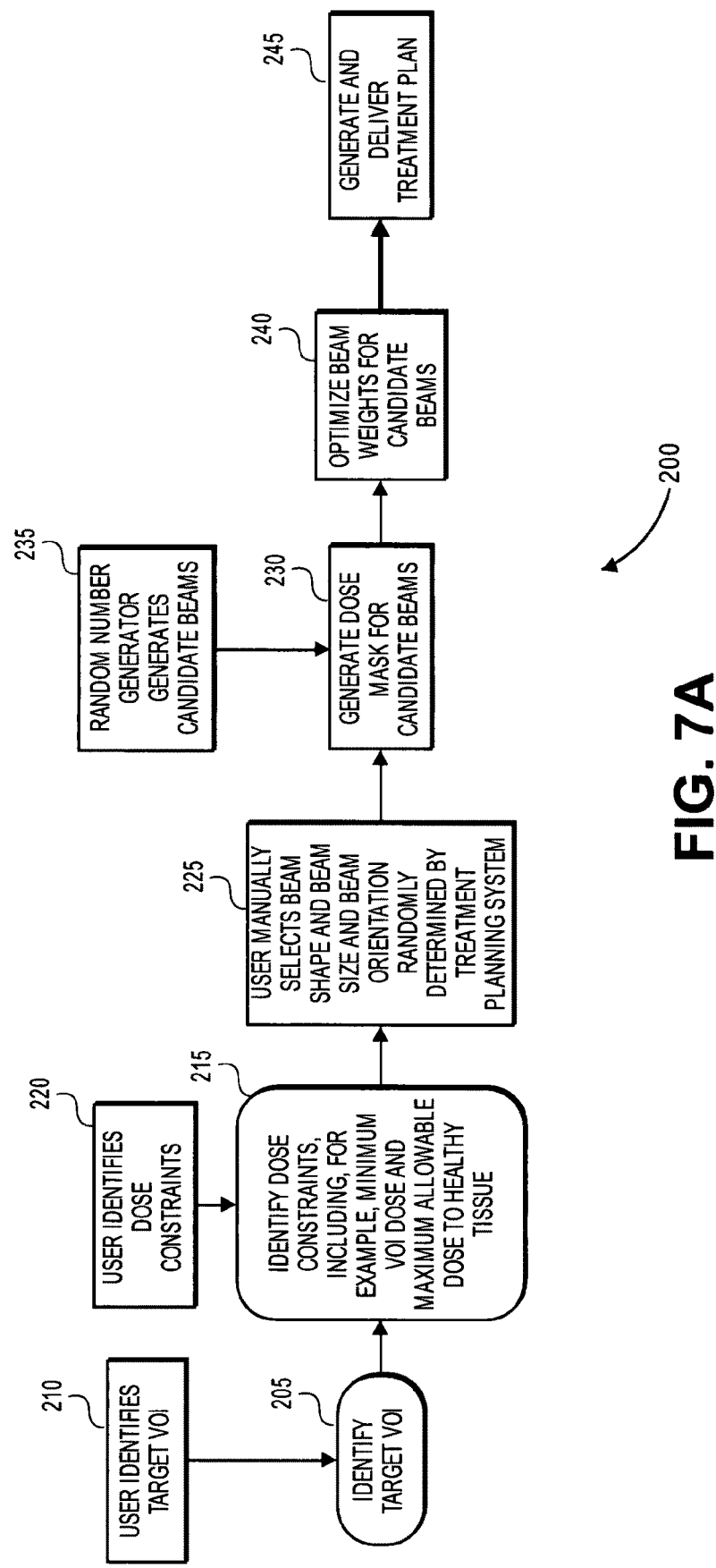
FIG. 7A is a flow chart of one implementation of a treatment planning algorithm.
Figure 7B:
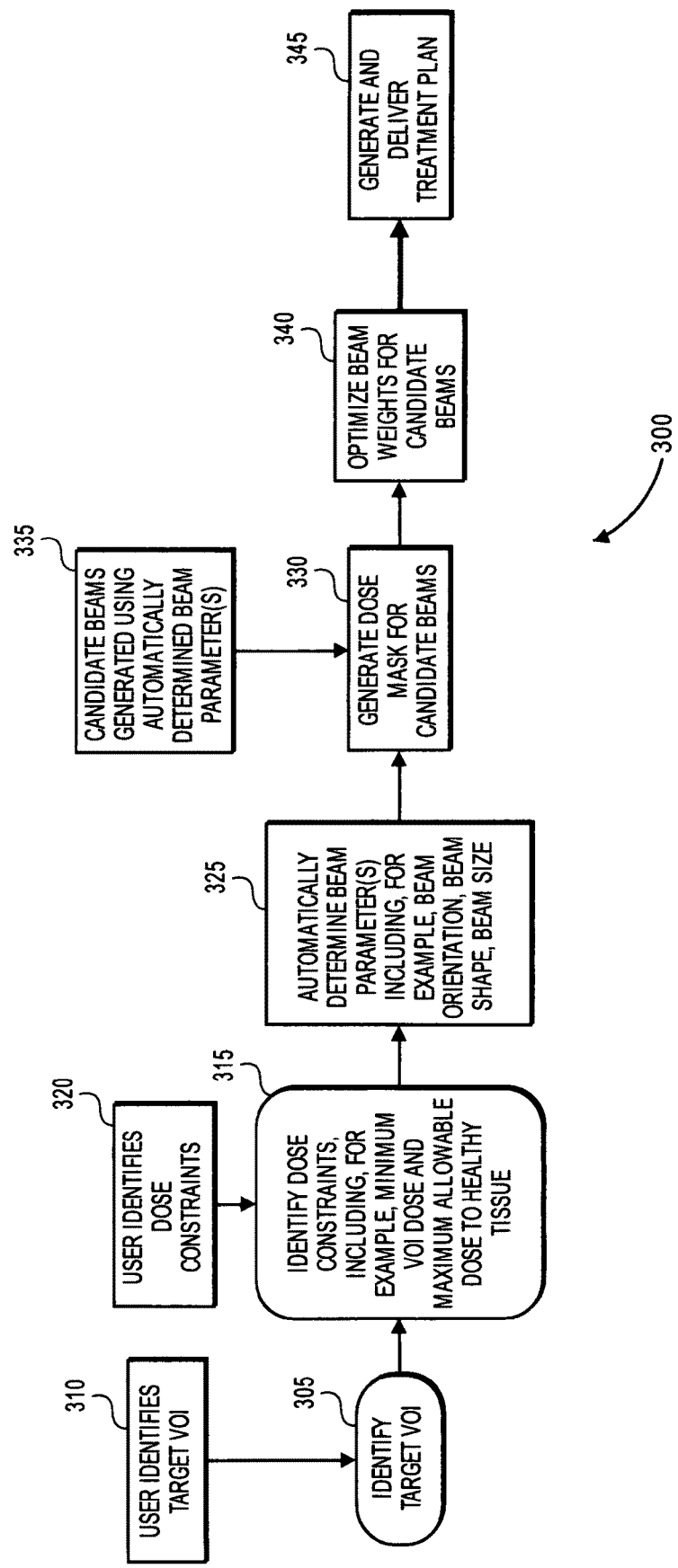
FIG. 7B is a flow chart of one implementation of a treatment planning algorithm in accordance with one embodiment of the invention.
Figure 7C:
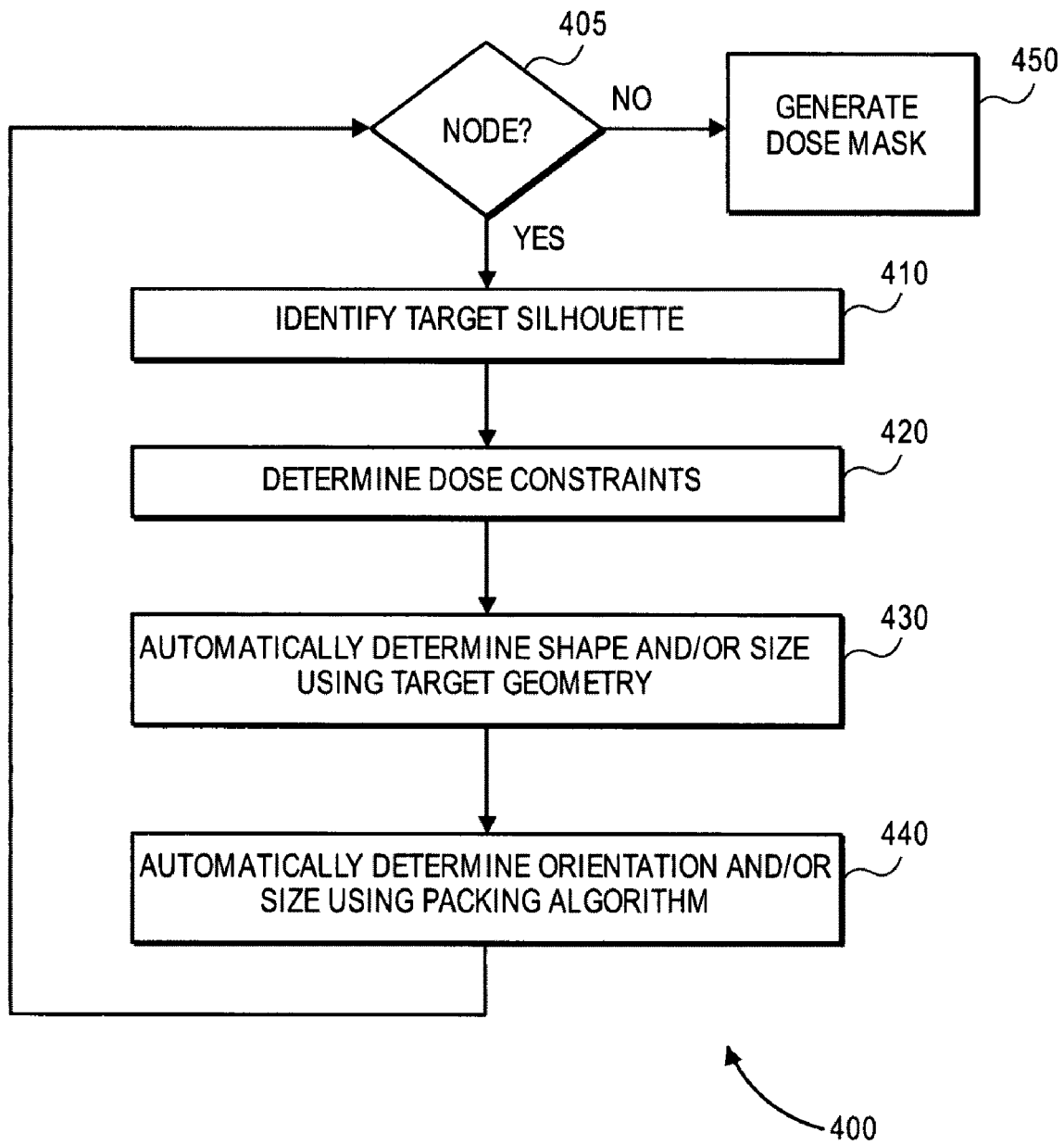
FIG. 7C is a flow chart showing pre-optimization at spatial nodes in accordance with one embodiment of the invention.

FIGS. 7A-7C illustrate exemplary algorithms for generating a treatment plan for use in a treatment planning system. In one embodiment, the algorithm is an iterative algorithm that optimizes deviations above the maximum dose constraint and below the minimum dose constraint. The iterative planning algorithm first generates a set of candidate beams and performs an initial dose distribution calculation, and subsequently attempts to improve the initial dose distribution calculation by altering the weight of one or more beams. In another embodiment, the algorithm performs convex optimization, such as, for example, the Simplex algorithm. One example of a cost function that may be optimized by convex optimization is the number of monitor units (linearly related to the total amount of time for which the treatment beam enabled) subject to the minimum/maximum dose constraints. The Simplex algorithm is well-known in the art. Alternatively, other iterative and non-iterative optimization algorithms may be used. In one embodiment, a combination of both algorithms may be used. In any event, the target delineation by the user is converted into a VOI bit mask (i.e., an overlay on the 3D image volume used for delineation, such that each position with the 3D image has a bit representing each VOI, set to '1' if the given VOI overlaps that image position, and '0' if it does not) for use with the treatment planning algorithm.

Typically, the treatment planning algorithms require target identification by the user. The treatment planning algorithm typically presents the user with a stack of 2D images which combine to represent the patient's 3D treatment area, and requires the user to identify contours on the 2D images which are then combined to define the 3D target volume (target VOI). In one embodiment, target identification includes a combination of edge detection and conversion of the edge to a series of points in image space. This series of points may then be combined to generate a 3D structure which is rendered on top of a 3D image. Edge detection is described in further detail in Delp et al., "Edge Detection Using Contour Tracing," Center for Robotics and Integrated Manufacturing, Robot System Division, College of Engineering, University of Michigan RSD-TR-12-83 (1983) 43. Contouring of points is described in further detail in Mat, Ruzinoor Che, "Evaluation of Silhouette Rendering Algorithms in Terrain Visualisation," MSC Computer Graphics and Virtual Environment Dissertation, Computer Science Department, The University of Hull (http:staf.uum.edu.my/ruzinoor/dissertation.htm). Other well-known methods for target identification may be used in the treatment planning algorithms.

FIG. 7A shows a process 200 for generating a treatment plan. In the implementation illustrated in FIG. 7A, the process 200 begins by delineating a target VOI (block 205). In the implementation of FIG. 7A, the user identifies the target, and the system creates the target VOI (block 210). For brevity, we hereafter refer to this process as "the user identifying the target VOI", and similarly for the user identifying the critical structure VOIs.

The process 200 continues at block 215 by identifying dose constraints. The dose constraints include, for example but not limited to: minimum target VOI dose, maximum allowable dose to healthy tissue, degree of homogeneity, degree of conformality, total beam on time, a total number of monitor units and a number of beams. In the implementation of FIG. 7A, the user also identifies the dose constraints (block 220). Alternatively, a user may first identify dose constraints and then identify the target VOI, or the user may identify some dose constraints, identify the target VOI, and then identify other dose constraints.

The process 200 continues at block 225 where the user manually selects the beam shape and beam size. It will be appreciated that by manually selecting the beam shape and beam size, the user is manually selecting the collimator(s) to be used in the treatment delivery. The beam orientation is randomly determined by the treatment planning algorithm. The treatment planning algorithm may use a random number generator in combination with the VOI bit mask to identify orientations which result in a beam will intersect an internal or surface point in the VOI.

The process continues at block 230 where a dose mask is generated for candidate beams. A dose mask is a representation of the amount of radiation dose delivered by the beam to a set of locations in space, normalized to the duration of the beam. One example element in a dose mask would be a voxel location, say (128, 203, 245) in a CT image of the patient, and a dose value of 1 cGy per second of beam on time. Any well-known process for generating a dose mask may be used. In the implementation of FIG. 7A, the candidate beams are randomly generated (block 235). The treatment planning algorithm may use a random number generator in combination with the number of available beams, sizes, positions, orientations, or combinations thereof to generate the candidate beam set. At block 240, beam weights are optimized for candidate beams. Any well-known process for optimizing beam weights may be used. As discussed above, the dose calculation and/or beam optimization may be an iterative, convex or combination algorithm.

The process 200 ends at block 245 where the treatment plan is generated. The treatment plan may be subsequently delivered to the patient using a radiation treatment system. In one embodiment, the radiation treatment system is the radiation treatment system 100 described above with reference to FIG. 5.

FIG. 7B shows another process 300 for generating a treatment plan in accordance with one embodiment of the invention. In the implementation illustrated in FIG. 7B, the process begins by identifying a target VOI (block 305). In the implementation of FIG. 7B, the user identifies the target VOI (block 310), as described above. The process continues at block 315 by identifying dose constraints. The dose constraints include, for example but not limited to: minimum VOI dose, maximum allowable dose to healthy tissue, degree of homogeneity, degree of conformality, total beam on time, a total number of monitor units and a number of beams. In the implementation of FIG. 7B, the user also identifies the dose constraints (block 320). Alternatively, a user may first identify dose constraints and then identify the target VOI, or the user may identify some dose constraints, identify the target VOL, and then identify other dose constraints.

The process continues at block 325 where one or more beam parameters are automatically determined. In one embodiment, the beam parameter(s) include, for example, one or more of the beam orientation, beam shape and beam size. Exemplary algorithms for automatically determining the one or more beam parameters are disclosed hereinafter. It will be appreciated that because the treatment planning algorithm automatically determines the beam parameter(s), the treatment planning algorithm can also automatically select one or more collimator sizes in order to best satisfy the dose constraints that have been applied. In one embodiment, the collimator(s) are fixed aperture collimator(s). In another embodiment, the collimator(s) are iris collimator(s). With an iris collimator, the shape of the collimator aperture is fixed, but the size of the aperture may be varied during the treatment session, either continuously or in fixed increments of size. In one embodiment, the IRIS collimator may be an IRIS collimator being developed by Deutsches Krebsforschungszentrum (DKFZ, German Cancer Research Center in the Helmholtz Association) of Heidelberg, Germany.

The process continues at block 330 where a dose mask is generated for candidate beams. Any well-known process for generating a dose mask may be used. In the implementation of FIG. 7B, the candidate beams are determined using the beam parameter(s) determined at block 325. The candidate beams may also be determined using the dose constraints and VOI bit mask. At block 340, beam weights are optimized for the candidate beams. Any well-known process for optimizing beam weights may be used. As described above, the dose calculation and/or beam optimization may be an iterative, convex or combination algorithm.

The process 300 ends at block 345 where the treatment plan is generated. The treatment plan may be subsequently delivered to the patient using a radiation treatment system. In one embodiment, the radiation treatment system is the radiation treatment system 100 described above with reference to FIG. 5.

FIG. 7C shows an iterative process 400 for automatically determining one or more beam parameter(s) in accordance with one embodiment of the invention. As shown in FIG. 7C, the process 400 determines at block 405 if a node needs to be analyzed. The nodes referred to in the process of FIG. 7C may be the spatial nodes 135 from FIG. 5. If a node needs to be analyzed (block 405), the target silhouette is identified at block 410, the dose constraints are determined at block 420, the shape and/or size are automatically determined using the geometry of the target at block 430, the orientation and/or size are automatically determined using a packing algorithm at block 440. The process returns to block 405 and repeats itself at each node until no nodes remain. When no nodes remain, the process continues to block 450 where the dose mask is generated.

Exemplary processes for determining shape and/or size using the target geometry and exemplary processes for determining orientation and/or size using a packing algorithm are disclosed hereinafter. It will also be appreciated that the iterative process of FIG. 7C may include fewer steps or more steps. For example, the iterative process may only include automatically determining one or more of the beam orientation, shape and size at each node. It will also be appreciated that the order of steps in the iterative process may vary. For example, the orientation and/or size may be determined using the packing algorithm before the shape and/or size are determined using the target geometry.

It will also be appreciated that the treatment planning algorithm may include a combination of user selection (FIG. 7A) and automatic determination (FIGS. 7B and 7C). For example, the user may manually select the beam size and beam shape, but the treatment planning algorithm automatically determines the beam orientation. In another example, the user manually selects the beam shape, and the treatment planning algorithm automatically determines the beam size and beam orientation. In addition, due to system constraints, the number of collimators may be fixed. Similarly, the collimator sizes may be fixed (e.g., a single collimator size) or restricted to a discrete set of sizes. Configurations having continuously variable-sized beams may be rounded to a nearest allowed collimator size(s).

As explained above with reference to FIGS. 7B and 7C, the treatment plan may include automatically determining one or more beam parameters. FIGS. 8A-10B illustrate an aspect of the exemplary algorithms for automatically determining beam parameter(s).

FIGS. 8A-8K illustrate an aspect of exemplary processes for automatically determining a beam parameter using a packing algorithm. The object used to pack the VOI in the packing algorithm of the radiation treatment planning system corresponds to a cross section of a radiation beam. The radiation beam, in turn, corresponds to the radiation profile produced by one or more collimator(s). Thus, the packing object defines one or more beam parameters. The beam parameter(s) can be used to automatically select one or more collimators. For example, the size of the packing object may define the size of the collimator, and the shape of the packing object may define the shape of the collimator. Similarly, the center of the packing shape may define the orientation of the collimator, with the orientation being defined by taking the line from the node to the center of the packing shape.

Packing algorithms, such as penny packing (for circles of equal size) or circle packing (for circles of varying size) algorithms, produce a set of circles that best fill an object, such as a target silhouette with non-overlapping circles. FIG. 8A shows a target (VOI) 500 having multiple circles 505 arranged in the VOI 500 according to a penny packing algorithm with no overlap allowed. Alternative packing algorithms find a set of overlapping circles whose union in the object. FIG. 8B illustrates an overlapping penny packing algorithm. In FIG. 8B, the circles 505 are arranged in the target 500 such that at least a portion of each circles overlaps another circle. It will be appreciated that the degree of overlap may vary from that shown in FIG. 8B. Exemplary circle packing algorithms are described at Collins et al., "A circle packing algorithm," Computational Geometry 25 (2003) 233-356, and Chen et al., "Algorithms for Congruent Sphere Packing and Applications," SCG '01 (2001) 212-221. Alternatively, other packing algorithms known in the art may be used.

The circles (or other packing objects) may be a fixed size or multiple sizes. FIG. 8C illustrates that packing objects of different sizes may be used by the packing algorithm. FIG. 8C shows the VOI 500 having a circle 510 having a first size, circles 515 having a second size and circles 520 having a third size. In FIG. 8C, circle 510 is larger than circles 515, which are larger than circles 520. It will be appreciated that fewer than three or greater than three sizes may be used by the packing algorithm and that the size may vary from the sizes illustrated.

The size of the objects used in the packing algorithm may be determined by examining the cross section of the predicted dose distribution (e.g., as represented by a dose mask) for a given collimator size. For example, taking the cross section of the dose mask for a beam with 30 mm collimator diameter, and taking all elements in the cross section having a value of more than 1 cGy/second may give an approximation to a circle with radius 15 mm.

As explained above, the packing algorithm may be an overlapping algorithm. Medial axis transformation is an exemplary overlapping packing algorithm. A medial axis transformation is a locus of centers of maximal inscribed disks. A maximal inscribed disk is a disk with a radius equal to the distance to the nearest boundary point that is not fully contained in any other inscribed disk centered at any other point in the object. The union of the set of all maximal inscribed disks is the object itself (i.e., the VOI). The skeleton plus the radii of the maximal disks at all skeleton points is a symmetric axis transform. An exemplary medial axis transformation algorithm is described at Ge et al., "On the Generation of Skeletons from Discrete Euclidean Distance Maps." IEEE Transactions on Pattern Analysis and Machine Intelligence, Vol. 18, No. 11 (1996) 1055-1066. Alternatively, other medial axis transformation algorithms or non-overlapping algorithms known in the art may be used.

FIGS. 8D and 8E illustrate medial axis transformation with a VOI. FIG. 8D shows a VOI 500 having an irregular geometry with a skeleton 525 therein formed using a medial axis transformation algorithm. FIG. 8E illustrates the medial axis transformation algorithm with a simple target geometry. It will be appreciated that medial axis transformation algorithms may be used with more complex target geometry as well; a simple target geometry is merely used for ease of description. In FIG. 8E, the VOI 500a includes a skeleton 525a. Circles 505a are arranged along the skeleton 525a. The skeleton 525a is used to determine the set of possible circles 505a. The algorithm, based on the dose constraints, then decides which of those circles 505a can be used to satisfy the dose constraints. For example, if the algorithm identifies 100 circles 505a, the algorithm may only pick five of the circles 505a, and hence corresponding collimator sizes and orientations, for treatment purposes. In addition, a maximum amount of overlap can be identified, and/or a maximum amount of uncovered area can be defined by the user or calculated based on the dose constraints, such as homogeneity, maximum dose amount and conformality, to eliminate some of the circles 505a.

FIG. 8F shows a VOI 500 having a first outline of the target silhouette 530 and a second outline of the target silhouette 540. The first outline of the target silhouette 530, as opposed to the actual silhouette 500, can be used by the packing algorithm if the user desires, for example, conformality. The second outline of the target silhouette 540, as opposed to the actual silhouette 500, can be used by the packing algorithm if the user desires, for example, dose homogeneity.

FIG. 8G illustrates the application of erosion and dilation of a beam to a packing algorithm. In FIG. 8G, the VOI 500b includes circles 505b, each circle having a first outline of the circle 530b and a second outline of the circle 540b. The first outline 530b corresponds to erosion and the second outline 540b corresponds to dilation of the radiation beam. Erosion and dilation allow overlapping packing algorithms to become non-overlapping algorithms and non-overlapping algorithms to become overlapping algorithms, respectively.

FIG. 8H-K illustrate packing algorithms with packing objects having different shapes and combinations of shapes. In one embodiment, the shape of the packing object is a geometric primitive (i.e., the shape of the collimator is a geometric primitive). Exemplary geometric primitives include, for example, circles, ellipses, hexagons, regular polygons and irregular polygons (e.g., a trapezium).

Figure 8H:
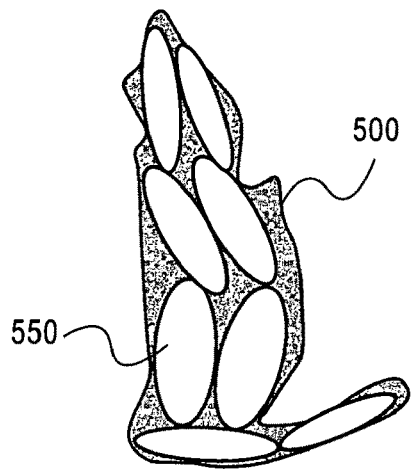
Figure 8I:
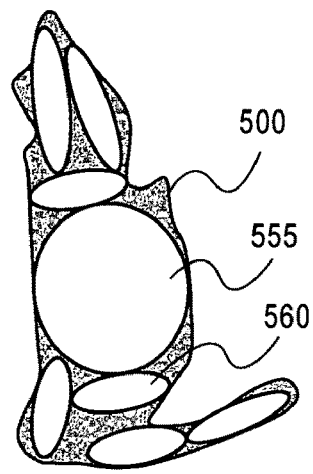
Figure 8J:
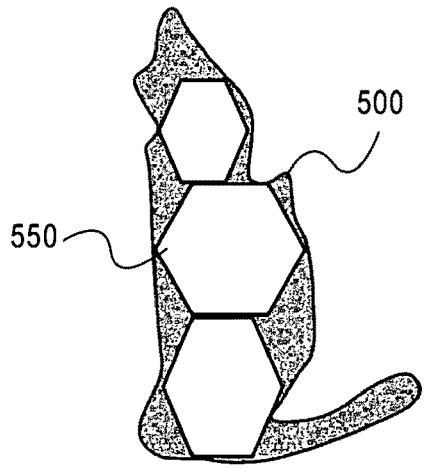
Figure 8K:
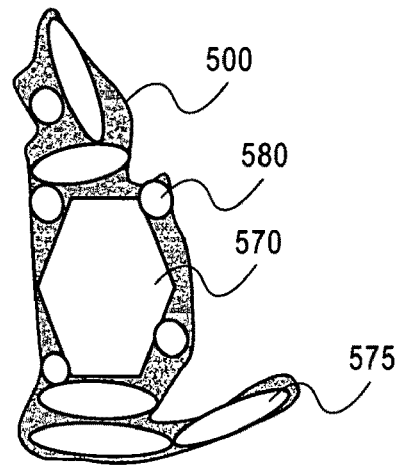

FIG. 8H shows a VOI 500 packed with ellipses 500, corresponding to an elliptically shaped radiation beam (i.e., elliptically shaped collimator). FIG. 8I shows a VOI 500 packed with a circle 555 and ellipses 560. FIG. 8J shows the target 500 packed with hexagons 565. FIG. 8K shows the target 500 packed with a hexagon 570, ellipses 575 and circles 580. It will be appreciated that the types of shapes, combinations of shapes, etc., used in the treatment planning algorithm may vary from those illustrated in FIGS. 8H-8K.

As shown in FIGS. 8A-8H, the use of collimator(s) of different sizes and/or shapes and/or at different orientations can be particularly advantageous with irregularly shaped targets. For example, a large collimator can deliver dose rapidly to the central part of the target while smaller collimators can deliver dose to conform to the irregular shape of the periphery. In addition, the use of collimator(s) of different sizes and/or shapes and/or at different orientations can result in more effective treatment planning.

Figure 9A:
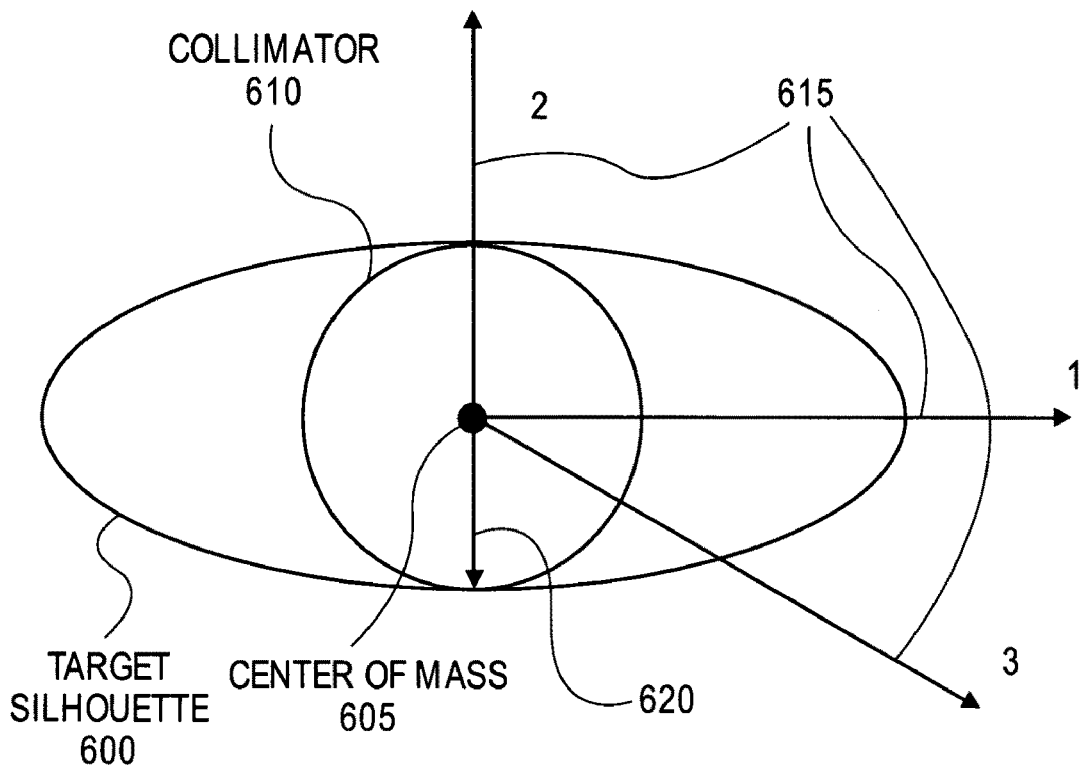
FIGS. 9A-9B are schematic views illustrating pre-optimization algorithms in accordance with embodiments of the invention.
Figure 9B:
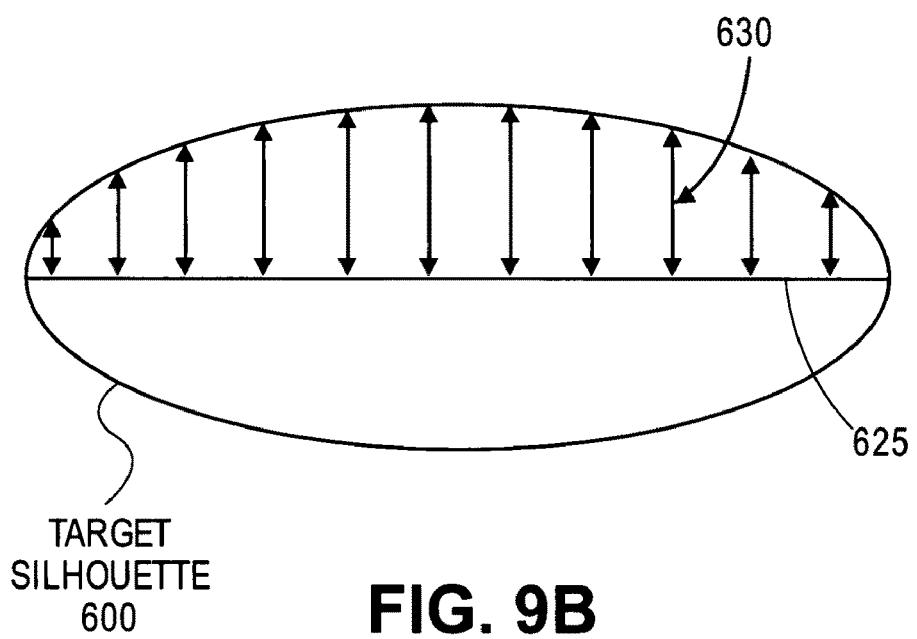

FIGS. 9A and 9B illustrate exemplary algorithms in which one or more beam parameters are automatically determined using the geometry of the target (VOI) 600. An exemplary algorithm is disclosed in Alpert et al., "The Principal Axes Transformation—A Method for Image Registration." J Nucl Med 1990; 31:1717-1722. As discussed above, the beam parameters lead to the selection of one or more collimators. The collimator may be selected as a function of a characteristic geometric dimension and/or a characteristic measure of shape. Various measures of shape can be used, including the ratio of minimum and maximum principal axis, various measures of eccentricity, and surface-to-volume ratio (with or without normalization to the surface-to-volume ratio of a sphere of identical volume).

FIG. 9A shows the VOI 600 having a center of mass 605. A collimator is shown in the center of the target 600 at the center of mass 605. A coordinate system 615 is shown, originating from the center of mass 605. In one embodiment, the collimator is selected as a specific percentage of a characteristic geometric dimension. For example, the primary axes (principal axes) of the user-delineated target are determined, and the collimator is selected as a specific percentage of the smallest principal axis. In the illustrated embodiment, the principal axes are represented by the coordinate system 615 and the smallest principal axis is represented by the axis 620. In one embodiment, the collimator size may be 100%-200% of the smallest principal axis. It will be appreciated that the collimator size may also be less than 100% of the smallest principal axis.

FIG. 9B shows an axis 625 through the center of the target 600. A plurality of axes 630 are shown perpendicular to the axis 625. In one embodiment, the axes 630 are used in a root mean square analysis of the target 625. The root mean square analysis may be useful in identifying a beam size.

Figure 10A:
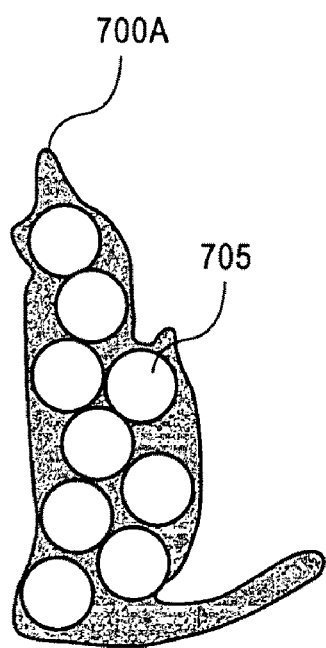
FIGS. 10A-10B are schematic views illustrating pre-optimization algorithms in accordance with embodiments of the invention.
Figure 10B:
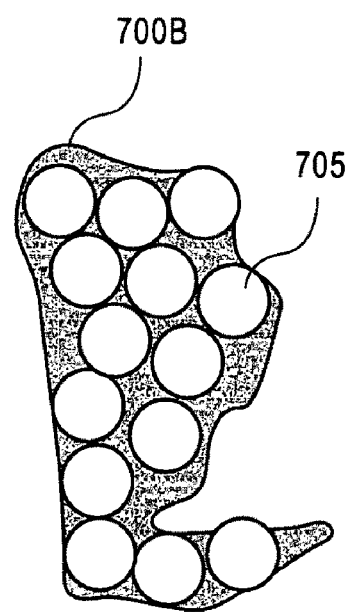

The treatment planning algorithm analyzes the VOI from each node position to find the one or more collimator sizes such that geometric primitives (i.e., packing object shape) of one or more characteristic sizes (e.g., circles of one or more diameters), corresponding to the available collimators, optimally fill or pack the VOI subject to the dose constraints. FIGS. 10A and 10B show a target (VOI) from two different node positions. FIG. 10A shows the VOI 700a from a first position, and FIG. 10B shows the VOI 700b from a second position. The same VOI has different shapes depending on the position. Both VOIs 700a and 700b are shown packed with circles 705, but the VOI 700b is more efficiently packed than the VOI 700a. As described above, the shape of the packing object and its size correspond to the collimator shape and size, and its position in the VOI corresponds to the beam orientation used to generate the candidate beams at each node position.

Figure 11A:
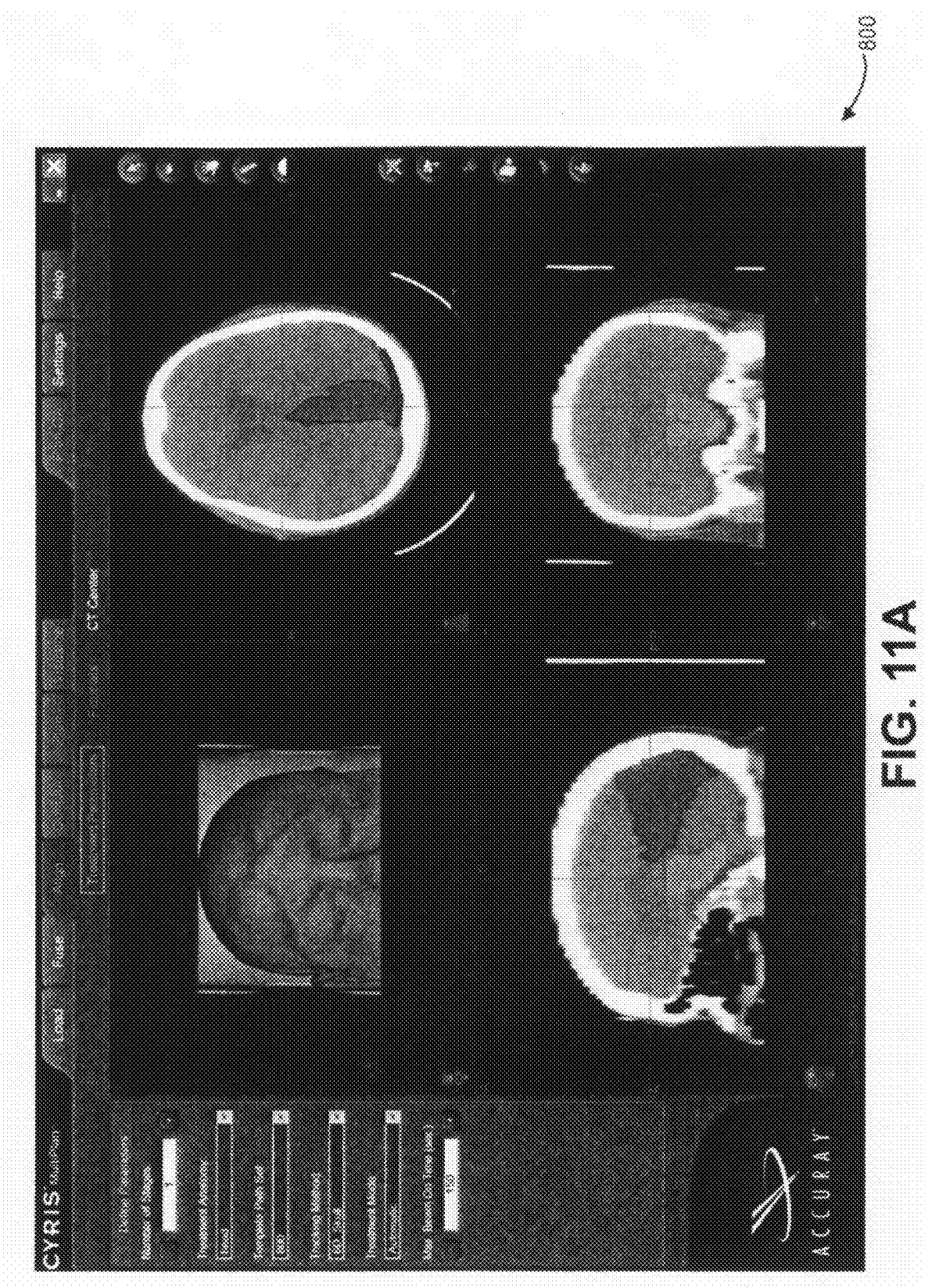
FIGS. 11A-E are screen shots of a user interface corresponding to a treatment planning algorithm in accordance with one embodiment of the invention.
Figure 11B:
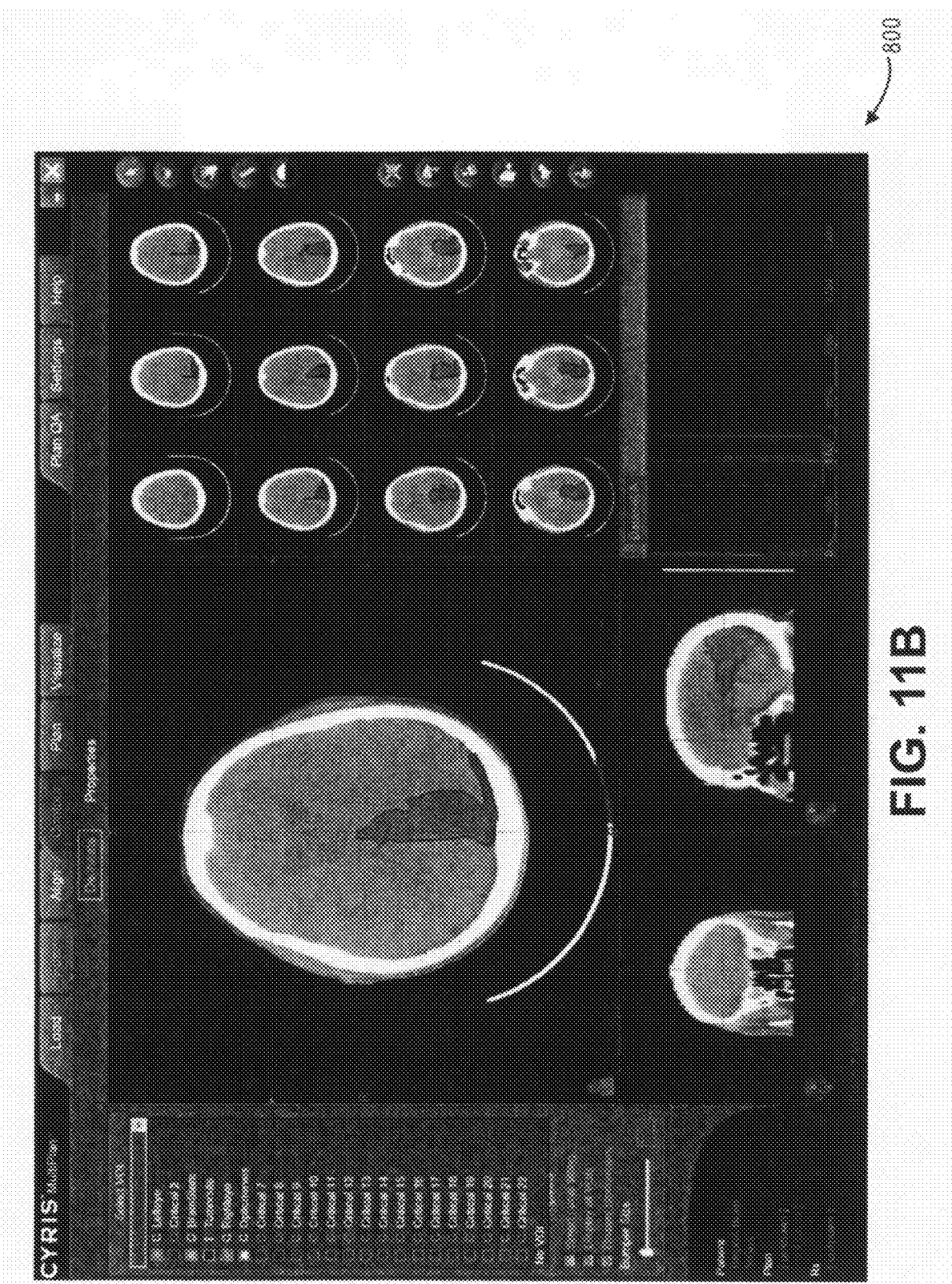
Figure 11C:
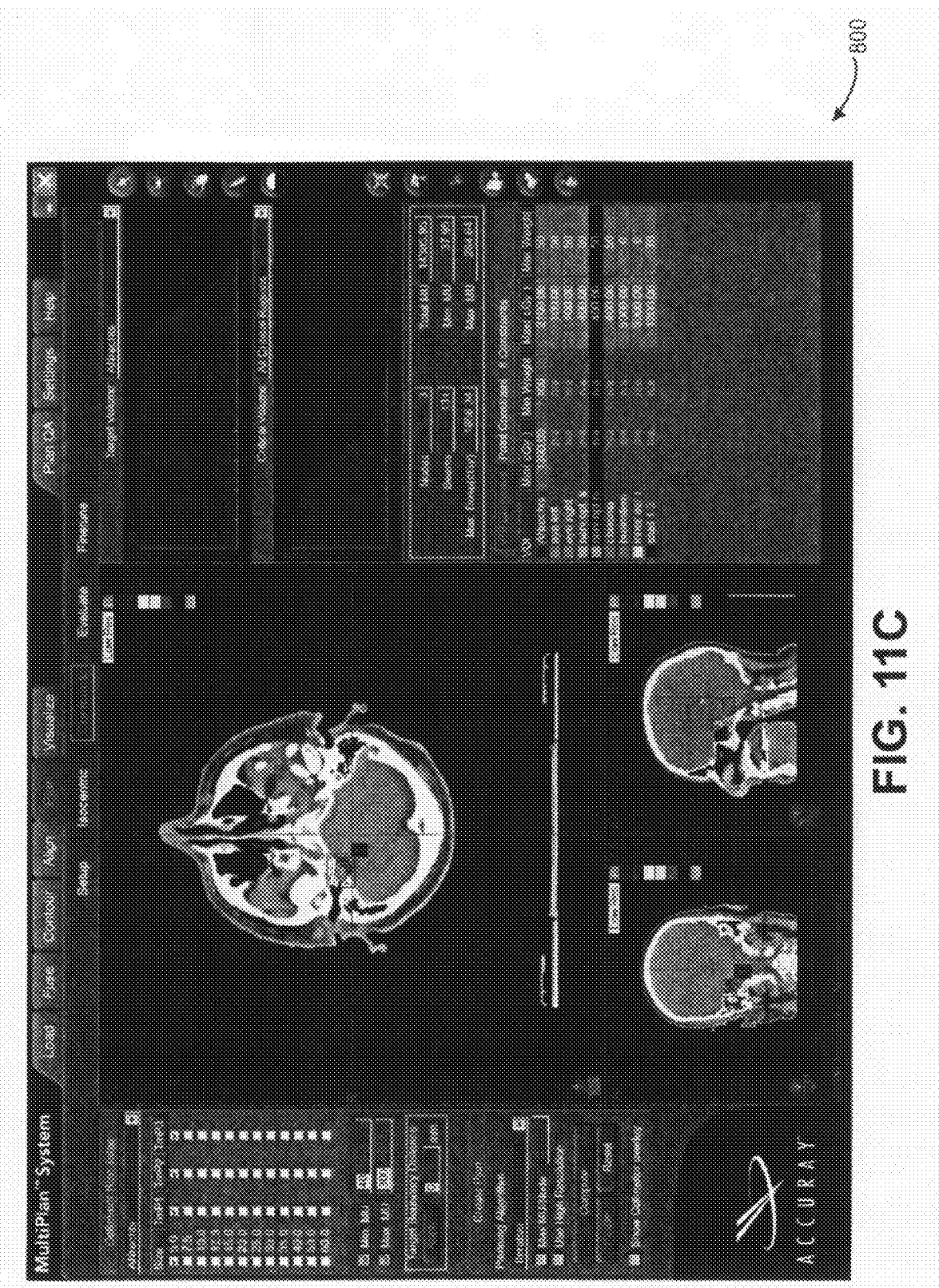
Figure 11D:
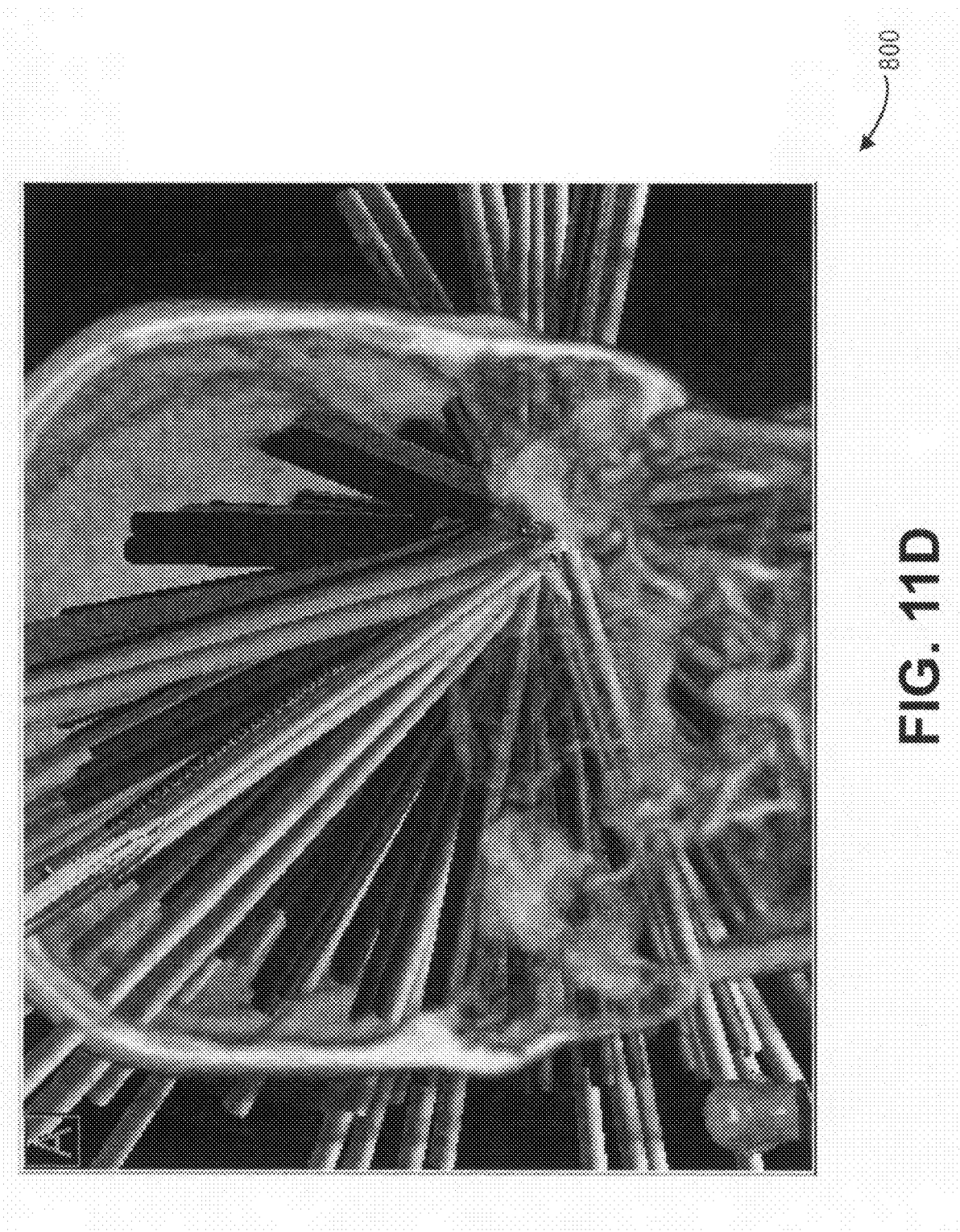
Figure 11E:
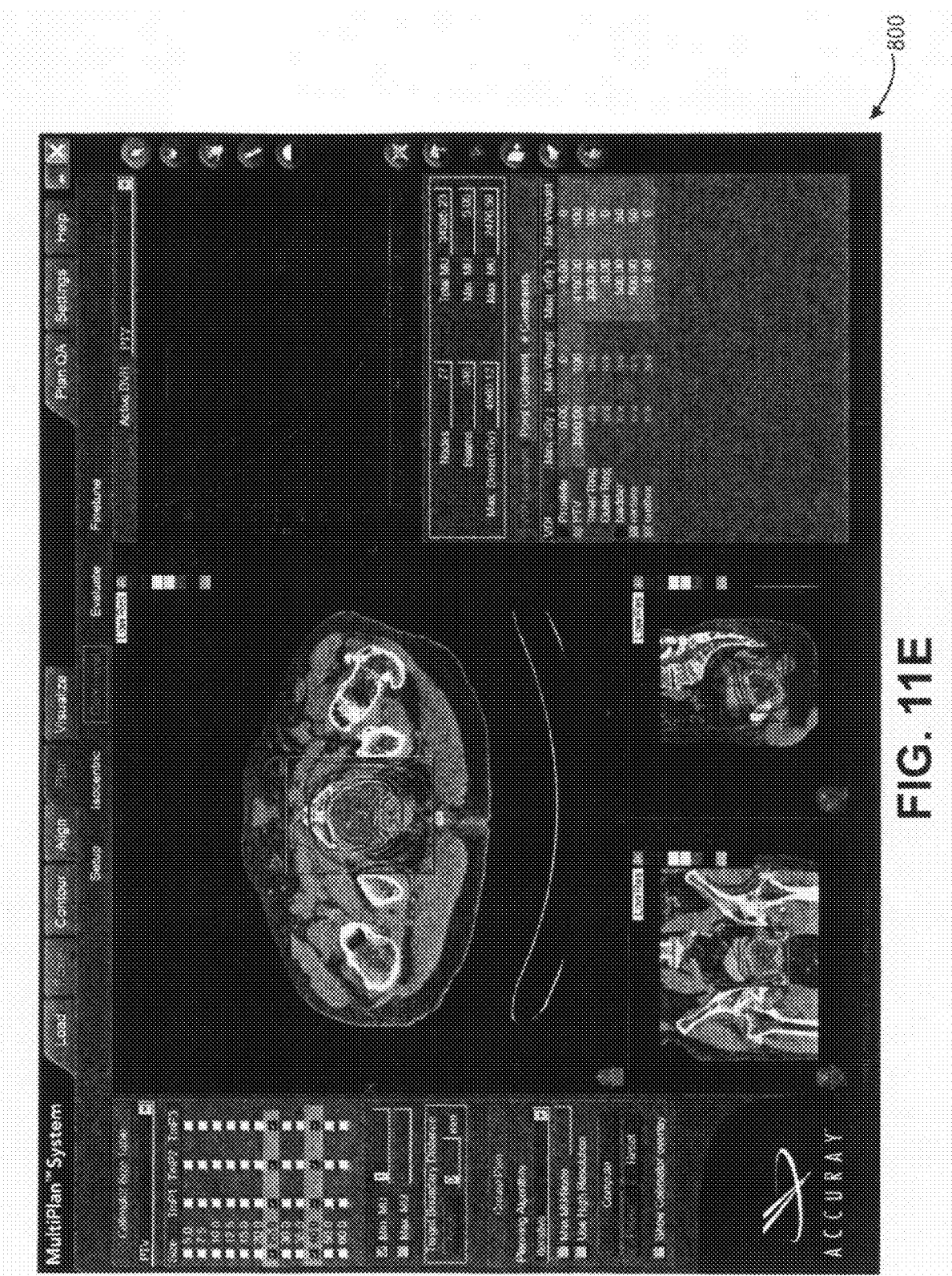

FIGS. 11A-E are exemplary screen shots of a user interface 800 for a treatment planning system. It will be appreciated that the user interface and screen shots may vary from those illustrated and described. As shown in FIG. 11A, images of the treatment region are loaded into the treatment planning system. FIG. 11B shows different 2D image slices containing cross sections of the target. As shown in FIG. 11C, the user may enter various dose constraints, as described above, into the user interface 800. FIG. 11D shows a treatment plan for the target generated using an algorithm described herein. FIG. 11E shows a treatment plan for the target, in which the collimator sizes are automatically selected. Alternatively, the user may be presented with suggested collimator size(s), and can accept and/or modify the suggested collimator size(s).

Figure 12:
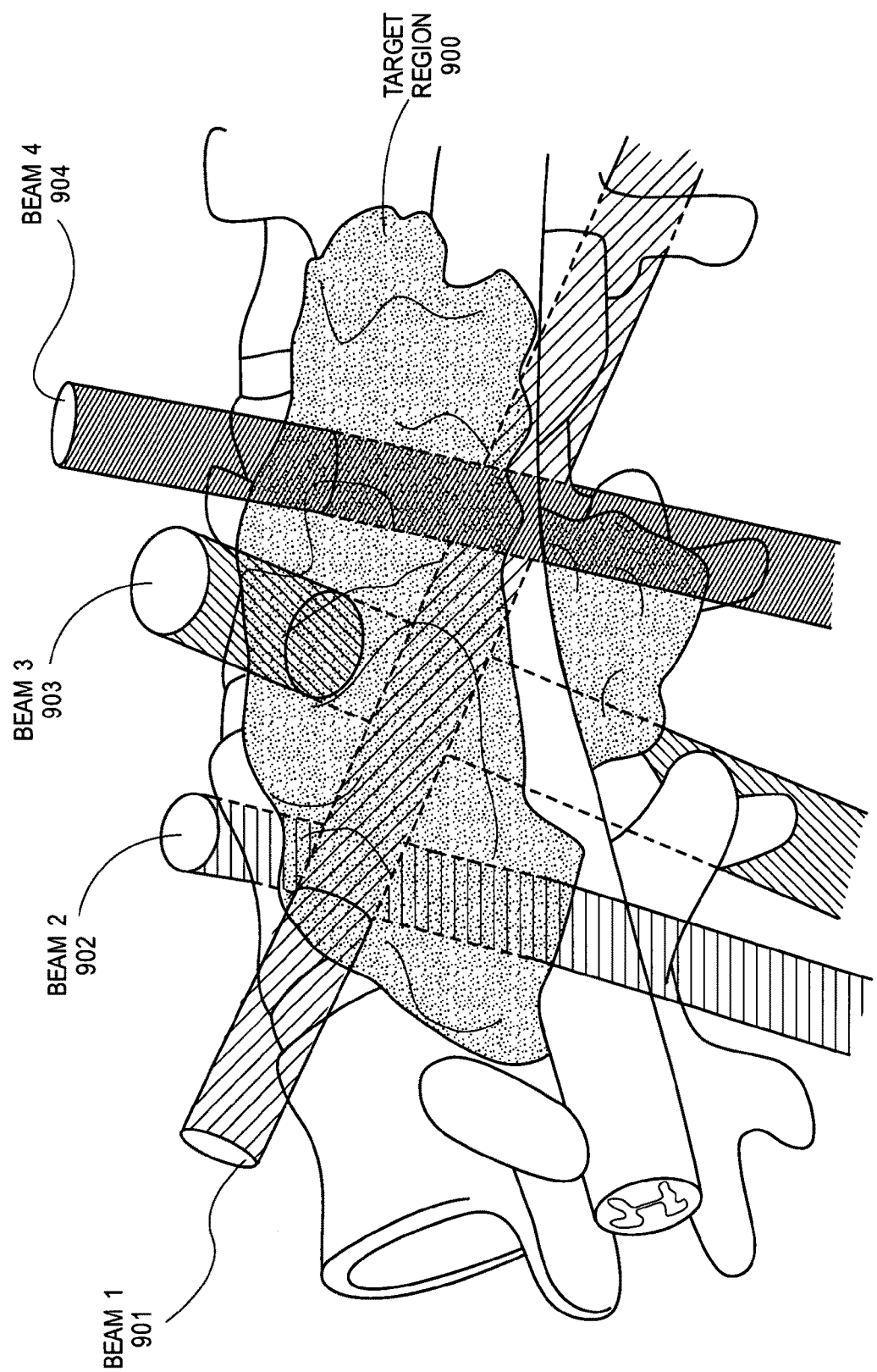
FIG. 12 is a perspective view of a non-isocentric radiation beam delivery at a pathological anatomy in accordance with one embodiment of the invention.

It should be noted that embodiments of the present invention may be used with either, or both, forward and inverse planning techniques (e.g., isocentric and non-isocentric, or conformal, beam geometries) to develop a treatment plan. FIG. 12 illustrates a two-dimensional perspective of non-isocentric radiation beam delivery at a target region based on conformal planning. It should be noted that four beams, beam_1 901, beam_2 902, beam_3 903, and beam_4 904 are illustrated in FIG. 12 only for ease of discussion and that an actual treatment plan may include more, or fewer, than four beams. Moreover, the four beams are representative of conformal planning, in which each beam passes through various points within target region 900 (e.g., the pathological anatomy). In conformal planning, some beams may or may not intersect or converge at a common point, and although the four beams appear to intersect in the perspective of FIG. 12, the beams may not intersect in their actual three-dimensional space. The radiation beams need only intersect with the target volume and do not necessarily converge on a single point, or isocenter, within the target 900. In one embodiment, conformal planning takes advantage of an image-guided, robotic-based radiation treatment system (e.g., for performing radiosurgery) such as the CyberKnife® system, because the LINAC positioning mechanism (e.g., robotic arm 3012 of FIG. 14) can move around freely with multiple degrees of freedom, allowing the radiation beams of the LINAC to point anywhere in space.

Figure 13:
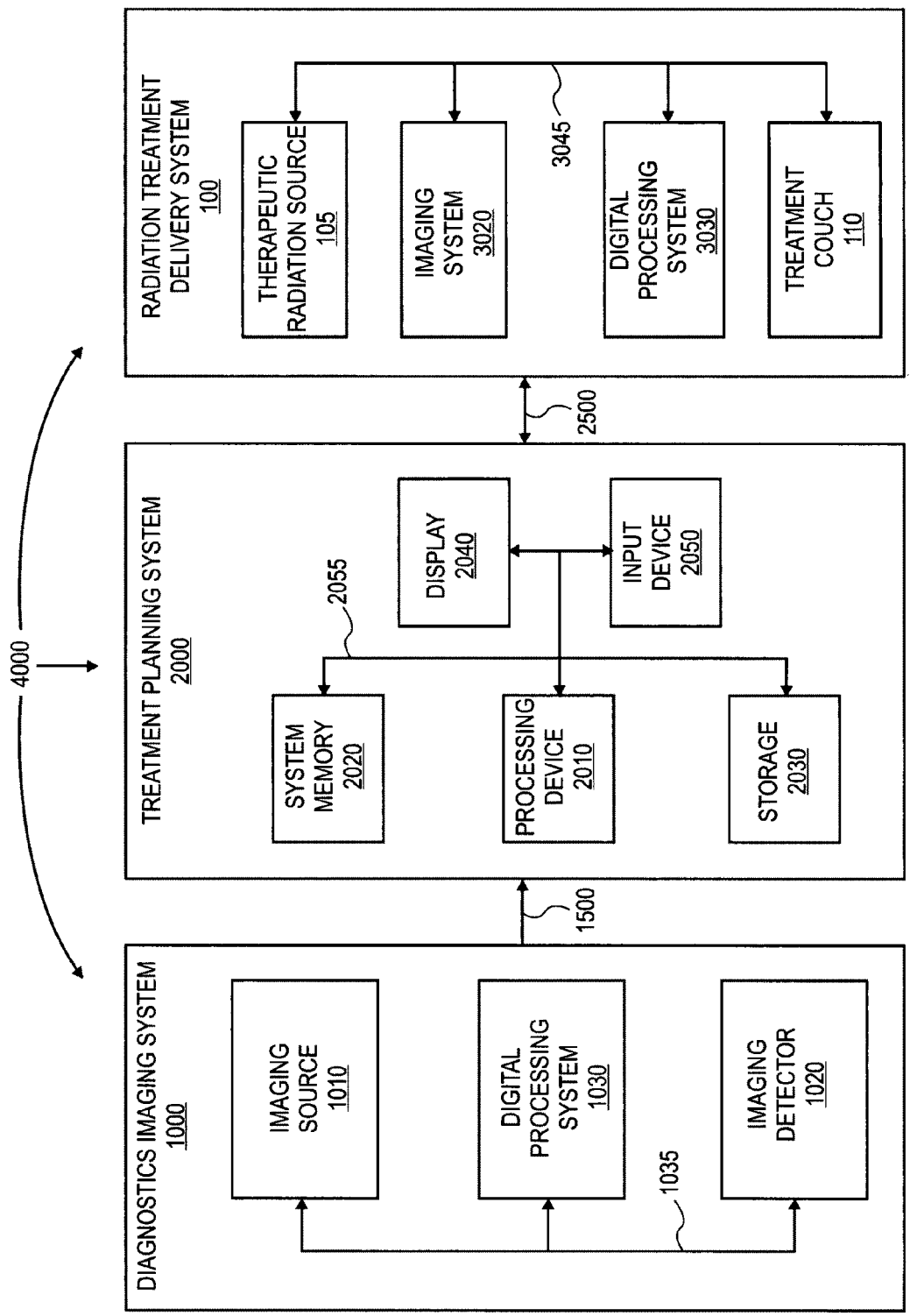
FIG. 13 is a block diagram of a system for diagnostic imaging and/or treatment delivery in accordance with one embodiment of the invention.

FIG. 13 illustrates one embodiment of systems that may be used to perform radiation treatment in which features of the present invention may be implemented. As described below and illustrated in FIG. 13, system 4000 may include a diagnostic imaging system 1000, a treatment planning system 2000, and a treatment delivery system 100. Diagnostic imaging system 1000 may be any system capable of producing medical diagnostic images of a treatment region in a patient that may be used for subsequent medical diagnosis, treatment planning and/or treatment delivery. For example, diagnostic imaging system 1000 may be a computed tomography (CT) system, a magnetic resonance imaging (MRI) system, a positron emission tomography (PET) system, an ultrasound system or the like. For ease of discussion, diagnostic imaging system 1000 may be discussed below at times in relation to a CT x-ray imaging modality. However, other imaging modalities such as those above may also be used.

Diagnostic imaging system 1000 includes an imaging source 1010 to generate an imaging beam (e.g., x-rays, ultrasonic waves, radio frequency waves, etc.) and an imaging detector 1020 to detect and receive the beam generated by imaging source 1010, or a secondary beam or emission stimulated by the beam from the imaging source (e.g., in an MRI or PET scan). In one embodiment, diagnostic imaging system 1000 may include two or more diagnostic X-ray sources and two or more corresponding imaging detectors. For example, two x-ray sources may be disposed around a patient to be imaged, fixed at an angular separation from each other (e.g., 90 degrees, 45 degrees, etc.) and aimed through the patient toward (an) imaging detector(s) which may be diametrically opposed to the x-ray sources. A single large imaging detector, or multiple imaging detectors, may also be used that would be illuminated by each x-ray imaging source. Alternatively, other numbers and configurations of imaging sources and imaging detectors may be used.

The imaging source 1010 and the imaging detector 1020 are coupled to a digital processing system 1030 to control the imaging operation and process image data. Diagnostic imaging system 1000 includes a bus or other means 1035 for transferring data and commands among digital processing system 1030, imaging source 1010 and imaging detector 1020. Digital processing system 1030 may include one or more general-purpose processors (e.g., a microprocessor), special purpose processor such as a digital signal processor (DSP) or other type of device such as a controller or field programmable gate array (FPGA). Digital processing system 1030 may also include other components (not shown) such as memory, storage devices, network adapters and the like. Digital processing system 1030 may be configured to generate digital diagnostic images in a standard format, such as the DICOM (Digital Imaging and Communications in Medicine) format, for example. In other embodiments, digital processing system 1030 may generate other standard or non-standard digital image formats. Digital processing system 1030 may transmit diagnostic image files (e.g., the aforementioned DICOM formatted files) to treatment planning system 2000 over a data link 1500, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treatment plan despite the existence of a physical separation between the system user and the patient.

Treatment planning system 2000 includes a processing device 2010 to receive and process image data. Processing device 2010 may represent one or more general-purpose processors (e.g., a microprocessor), special purpose processor such as a digital signal processor (DSP) or other type of device such as a controller or field programmable gate array (FPGA). Processing device 2010 may be configured to execute instructions for performing the operations of the treatment planning system 2000 discussed herein that, for example, may be loaded in processing device 2010 from storage 2030 and/or system memory 2020.

Treatment planning system 2000 may also include system memory 2020 that may include a random access memory (RAM), or other dynamic storage devices, coupled to processing device 2010 by bus 2055, for storing information and instructions to be executed by processing device 2010. System memory 2020 also may be used for storing temporary variables or other intermediate information during execution of instructions by processing device 2010. System memory 2020 may also include a read only memory (ROM) and/or other static storage device coupled to bus 2055 for storing static information and instructions for processing device 2010.

Treatment planning system 2000 may also include storage device 2030, representing one or more storage devices (e.g., a magnetic disk drive or optical disk drive) coupled to bus 2055 for storing information and instructions. Storage device 2030 may be used for storing instructions for performing the treatment planning methods discussed herein.

Processing device 2010 may also be coupled to a display device 2040, such as a cathode ray tube (CRT) or liquid crystal display (LCD), for displaying information (e.g., a two-dimensional or three-dimensional representation of the VOI) to the user. An input device 2050, such as a keyboard, may be coupled to processing device 2010 for communicating information and/or command selections to processing device 2010. One or more other user input devices (e.g., a mouse, a trackball or cursor direction keys) may also be used to communicate directional information, to select commands for processing device 2010 and to control cursor movements on display 2040.

It will be appreciated that treatment planning system 2000 represents only one example of a treatment planning system, which may have many different configurations and architectures, which may include more components or fewer components than treatment planning system 2000 and which may be employed with the present invention. For example, some systems often have multiple buses, such as a peripheral bus, a dedicated cache bus, etc. The treatment planning system 2000 may also include MIRIT (Medical Image Review and Import Tool) to support DICOM import (so images can be fused and targets delineated on different systems and then imported into the treatment planning system for planning and dose calculations), expanded image fusion capabilities that allow the user to treatment plan and view dose distributions on any one of various imaging modalities (e.g., MRI, CT, PET, etc.). Treatment planning systems are known in the art; accordingly, a more detailed discussion is not provided.

Treatment planning system 2000 may share its database (e.g., data stored in storage device 2030) with a treatment delivery system, such as treatment delivery system 100, so that it may not be necessary to export from the treatment planning system prior to treatment delivery. Treatment planning system 2000 may be linked to treatment delivery system 100 via a data link 2500, which may be a direct link, a LAN link or a WAN link as discussed above with respect to data link 1500. It should be noted that when data links 1500 and 2500 are implemented as LAN or WAN connections, any of diagnostic imaging system 1000, treatment planning system 2000 and/or treatment delivery system 100 may be in decentralized locations such that the systems may be physically remote from each other. Alternatively, any of diagnostic imaging system 2000, treatment planning system 2000 and/or treatment delivery system 100 may be integrated with each other in one or more systems.

Treatment delivery system 100 includes a therapeutic and/or surgical radiation source 105 to administer a prescribed radiation dose to a target volume in conformance with a treatment plan. Treatment delivery system 100 may also include an imaging system 3020 to capture intra-treatment images of a patient volume (including the target volume) for registration or correlation with the diagnostic images described above in order to position the patient with respect to the radiation source. Treatment delivery system 100 may also include a digital processing system 3030 to control radiation source 105, imaging system 3020, and a patient support device such as a treatment couch 110. Digital processing system 3030 may include one or more general-purpose processors (e.g., a microprocessor), special purpose processor such as a digital signal processor (DSP) or other type of device such as a controller or field programmable gate array (FPGA). Digital processing system 3030 may also include other components (not shown) such as memory, storage devices, network adapters and the like. Digital processing system 3030 may be coupled to radiation source 105, imaging system 3020 and treatment couch 110 by a bus 3045 or other type of control and communication interface.

Figure 14:
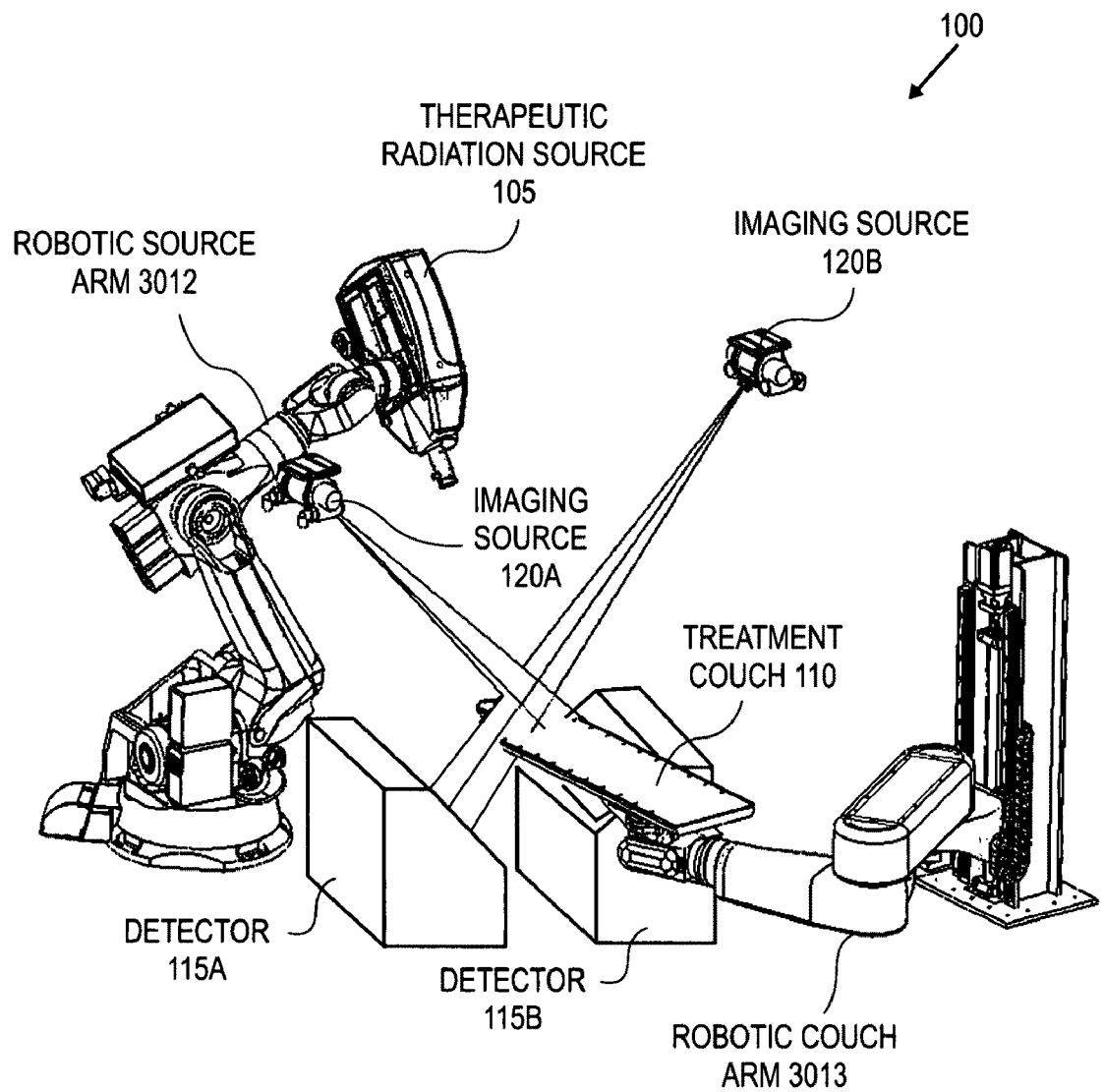
FIG. 14 is a perspective view of a system for diagnostic imaging and/or treatment delivery in accordance with one embodiment of the invention.

In one embodiment, as illustrated in FIG. 14, treatment delivery system 100 may be an image-guided, robotic-based radiation treatment system (e.g., for performing radiosurgery) such as the CyberKnife® system developed by Accuray Incorporated of California. In FIG. 14, radiation source 105 may be represented by a linear accelerator (LINAC) mounted on the end of a robotic arm 3012 having multiple (e.g., 5 or more) degrees of freedom in order to position the LINAC to irradiate a pathological anatomy (target region or volume) with beams delivered from many angles in an operating volume (e.g., a sphere) around the patient. Treatment may involve beam paths with a single isocenter (point of convergence), multiple isocenters, or with a non-isocentric approach (i.e., the beams need only intersect with the pathological target volume and do not necessarily converge on a single point, or isocenter, within the target as illustrated in FIG. 12). Treatment can be delivered in either a single session (monofraction) or in a small number of sessions as determined during treatment planning. With treatment delivery system 100, in one embodiment, radiation beams may be delivered according to the treatment plan without fixing the patient to a rigid, external frame to register the intra-operative position of the target volume with the position of the target volume during the pre-operative treatment planning phase.

In FIG. 14, imaging system 3020 may be represented by X-ray sources 120A and 120B and X-ray image detectors (imagers) 115A and 115B. In one embodiment, for example, two x-ray sources 120A and 120B may be nominally aligned to project imaging x-ray beams through a patient from two different angular positions (e.g., separated by 90 degrees, 45 degrees, etc.) and aimed through the patient on treatment couch 110 toward respective detectors 115A and 115B. In another embodiment, a single large imager can be used that would be illuminated by each x-ray imaging source. Alternatively, other numbers and configurations of imaging sources and imagers may be used.

Digital processing system 3030 may implement algorithms to register (i.e., determine a common coordinate system for) images obtained from imaging system 3020 with pre-operative treatment planning images in order to align the patient on the treatment couch 110 within the treatment delivery system 100, and to precisely position the radiation source with respect to the target volume.

The treatment couch 110 may be coupled to another robotic arm (not illustrated) having multiple (e.g., 5 or more) degrees of freedom. The couch arm may have five rotational degrees of freedom and one substantially vertical, linear degree of freedom. Alternatively, the couch arm may have six rotational degrees of freedom and one substantially vertical, linear degree of freedom or at least four rotational degrees of freedom. The couch arm may be vertically mounted to a column or wall, or horizontally mounted to pedestal, floor, or ceiling. Alternatively, the treatment couch 110 may be a component of another mechanical mechanism, such as the Axum® treatment couch developed by Accuray Incorporated of California, or be another type of conventional treatment table known to those of ordinary skill in the art.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the effectuation of an operation controlled by the treatment planning system, such as the application of a beam (e.g., radiation, acoustic, etc.).

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

The invention claimed is:

1. A method comprising:
   automatically determining a beam parameter at each of a plurality of treatment nodes, wherein the beam parameter is a geometric primitive for a beam shape; and
   automatically calculating a dose distribution based on the beam parameter at each of the plurality of treatment nodes.

2. The method of claim 1 wherein the geometric primitive includes a circle.

3. The method of claim 1, wherein the geometric primitive includes an ellipse.

4. The method of claim 1, wherein the geometric primitive is a regular polygon.

5. The method of claim 1, wherein the geometric primitive is an irregular polygon.

6. The method of claim 1, wherein the beam shape is determined using a geometry of a target to be radiated.

7. The method of claim 1, further comprising determining a beam size.

8. The method of claim 7, wherein the beam size is determined using a geometry of a target to be radiated.

9. The method of claim 7, wherein the beam size is determined using a packing algorithm.

10. The method of claim 1, wherein the beam parameter comprises a beam orientation.

11. The method of claim 10, wherein the beam orientation is determined using a packing algorithm.

12. The method of claim 10, wherein the beam orientation is determined using a geometry of a target to be radiated.

13. The method of claim 1, further comprising automatically selecting one or more collimators based on the beam parameter.

14. A method of generating a treatment plan for a radiation delivery treatment system comprising:
    at a node position, stacking together radiation beams at different orientations to match a target silhouette;
    automatically determining a beam parameter at the node position; and
    generating the treatment plan based on at least the beam parameter.

15. The method of claim 14, wherein the beam parameter comprises a beam shape.

16. The method of claim 15, wherein the beam shape is a geometric primitive.

17. The method of claim 16, wherein the geometric primitive includes a circle.

18. The method of claim 16, wherein the geometric primitive includes an ellipse.

19. The method of claim 16, wherein the geometric primitive is a regular polygon.

20. The method of claim 16, wherein the geometric primitive is an irregular polygon.

21. The method of claim 16, wherein the beam shape is determined using a geometry of a target to be radiated.

22. The method of claim 14, wherein the beam parameter comprises a beam size.

23. The method of claim 22, wherein the beam size is determined using a geometry of a target to be radiated.

24. The method of claim 22, wherein the beam size is determined using a packing algorithm.

25. The method of claim 14, wherein the beam parameter comprises a beam orientation.

26. The method of claim 25, wherein the beam orientation is determined using a packing algorithm.

27. The method of claim 25, wherein the beam orientation is determined using a geometry of a target to be radiated.

28. The method of claim 14, further comprising automatically selecting one or more collimators based on the beam parameter.

29. A system comprising:
   means for automatically determining a beam parameter at each of a plurality of treatment nodes, wherein the beam parameter is a geometric primitive for a beam shape; and
   means for automatically calculating a dose distribution based on the beam parameter at each of the plurality of treatment nodes.

30. The system of claim 29, further comprising means for automatically determining a beam size.

31. A system for generating a treatment plan for a radiation delivery treatment system comprising:
   means for, at a node position, stacking together radiation beams at different orientations to match a target silhouette;
   means for automatically determining a beam parameter at the node position; and
   means for generating the treatment plan based on at least the beam parameter.

32. The system of claim 31, wherein the beam parameter is a beam size.

33. The system of claim 31, where the beam parameter is a beam shape.

34. An apparatus comprising:
   a radiation beam treatment system to deliver a radiation beam to a treatment site using a collimator; and
   a radiation treatment planning system operatively coupled to the radiation beam treatment system, the radiation treatment planning system to determine a beam parameter at each of a plurality of treatment nodes, wherein the beam parameter is a geometric primitive for a beam shape of the collimator, and automatically calculate a dose distribution based on the beam parameter at each of the plurality of treatment nodes.

35. An apparatus for generating a treatment plan for a radiation delivery treatment system comprising:
   a radiation beam treatment system to deliver a radiation beam to a treatment site; and
   a radiation treatment planning system operatively coupled to the radiation beam treatment system, the radiation treatment planning system to, at a node position, stack together radiation beams at different orientations to match a target silhouette, automatically determine a beam parameter at the node position, and generate the treatment plan based on at least the beam parameter.

36. The apparatus of claim 35, wherein the beam parameter is a beam size.

37. The apparatus of claim 35, where the beam parameter is a beam shape.

* * * * *